(12) United States Patent
Shmayahu et al.

(10) Patent No.: US 11,284,813 B2
(45) Date of Patent: Mar. 29, 2022

(54) REAL-TIME DISPLAY OF TISSUE DEFORMATION BY INTERACTIONS WITH AN INTRA-BODY PROBE

(71) Applicant: Navix International Limited, Road Town (VG)

(72) Inventors: Yizhaq Shmayahu, Ramat-HaSharon (IL); Yitzhack Schwartz, Haifa (IL)

(73) Assignee: Navix International Limited, Road Town (VG)

( * ) Notice: Subject to any disclaimer, the term of this patent is extended or adjusted under 35 U.S.C. 154(b) by 284 days.

(21) Appl. No.: 16/349,646

(22) PCT Filed: Nov. 16, 2017

(86) PCT No.: PCT/IB2017/057175
§ 371 (c)(1),
(2) Date: May 14, 2019

(87) PCT Pub. No.: WO2018/092062
PCT Pub. Date: May 24, 2018

(65) Prior Publication Data
US 2019/0328275 A1  Oct. 31, 2019

Related U.S. Application Data

(60) Provisional application No. 62/422,708, filed on Nov. 16, 2016, provisional application No. 62/422,713, (Continued)

(51) Int. Cl.
*A61B 5/06* (2006.01)
*A61B 34/20* (2016.01)
(Continued)

(52) U.S. Cl.
CPC .............. *A61B 5/064* (2013.01); *A61B 5/742* (2013.01); *A61B 34/20* (2016.02); *G06T 7/0012* (2013.01);
(Continued)

(58) Field of Classification Search
CPC ............ A61B 18/1492; A61B 18/1815; A61B 2018/00577; A61B 2018/00613;
(Continued)

(56) References Cited

U.S. PATENT DOCUMENTS

| | | |
|---|---|---|
| 4,917,097 A | 4/1990 | Proudian et al. |
| 5,553,611 A | 9/1996 | Budd et al. |

(Continued)

FOREIGN PATENT DOCUMENTS

| | | |
|---|---|---|
| CA | 2237992 | 3/1998 |
| EP | 0974936 | 1/2000 |

(Continued)

OTHER PUBLICATIONS

International Preliminary Report on Patentability dated May 31, 2019 From the International Bureau of WIPO Re. Application No. PCT/IB2017/057169. (9 Pages).
(Continued)

*Primary Examiner* — Amelie R Davis

(57) ABSTRACT

In some embodiments, data sensed and/or operational parameters used during a catheterization procedure are used in the motion frame-rate updating and visual rendering of a simulated organ geometry. In some embodiments, measurements of and/or effects on tissue by sensed and/or commanded probe-tissue interactions are converted into adjustments to the simulated organ geometry, allowing dynamic visual simulation of intra-body states and/or events based on optionally partial and/or non-visual input data. Adjustments to geometry are optionally to 3-D positions of simulated data
(Continued)

and/or to simulated surface properties affecting geometrical appearances (e.g., normal mapping). Optionally, the organ geometry is rendered as a virtual material using a software environment (preferably a graphical game engine) which applies simulated optical laws to material appearance parameters affecting the virtual material's visual appearance. Optionally, physiology, motion physics, and/or other physical processes are simulated based on live inputs, as part of assigning geometrical adjustments to the simulated tissue.

33 Claims, 16 Drawing Sheets

Related U.S. Application Data filed on Nov. 16, 2016, provisional application No. 62/422,705, filed on Nov. 16, 2016.

(51) Int. Cl.
  *A61B 5/00* (2006.01)
  *G06T 7/00* (2017.01)
  *A61B 90/00* (2016.01)
  *A61B 18/00* (2006.01)

(52) U.S. Cl.
  CPC ........... *A61B 2018/00577* (2013.01); *A61B 2034/2055* (2016.02); *A61B 2034/2065* (2016.02); *A61B 2034/2068* (2016.02); *A61B 2090/364* (2016.02); *G06T 2207/30096* (2013.01)

(58) Field of Classification Search
  CPC ...... A61B 2018/0212; A61B 2034/104; A61B 2034/2051; A61B 2034/2055; A61B 2034/2065; A61B 2034/2068; A61B 2034/252; A61B 2090/065; A61B 2090/364; A61B 34/10; A61B 34/20; A61B 5/064; A61B 5/742; A61N 7/02; G06T 2207/30096; G06T 7/0012
  See application file for complete search history.

(56) References Cited

U.S. PATENT DOCUMENTS

| | | |
|---|---|---|
| 5,598,848 A | 2/1997 | Swanson et al. |
| 5,662,108 A | 9/1997 | Budd et al. |
| 5,697,377 A | 12/1997 | Wittkampf |
| 5,724,978 A | 3/1998 | Tenhoff |
| 5,983,126 A | 11/1999 | Wittkampf |
| 6,019,725 A | 2/2000 | Vesely et al. |
| 6,038,468 A | 3/2000 | Rex |
| 6,240,307 B1 | 5/2001 | Beatty et al. |
| 6,266,552 B1 | 7/2001 | Slettenmark |
| 6,301,496 B1 † | 10/2001 | Reisfeld |
| 6,317,621 B1 | 11/2001 | Graumann et al. |
| 6,322,558 B1 | 11/2001 | Taylor et al. |
| 6,423,057 B1 | 7/2002 | He et al. |
| 6,515,657 B1 | 2/2003 | Zanelli |
| 6,640,119 B1 | 10/2003 | Budd et al. |
| 6,728,562 B1 | 4/2004 | Budd et al. |
| 6,826,420 B1 | 11/2004 | Beatty et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,989,010 B2 | 1/2006 | Francischelli et al. |
| 6,990,370 B1 | 1/2006 | Beatty et al. |
| 7,001,383 B2 | 2/2006 | Keidar |
| 7,146,210 B2 | 12/2006 | Palti |
| 7,187,973 B2 | 3/2007 | Hauck |
| 7,189,208 B1 | 3/2007 | Beatty et al. |
| 7,306,593 B2 † | 12/2007 | Keidar |
| 7,881,769 B2 | 2/2011 | Sobe |
| 7,996,060 B2 | 8/2011 | Trofimov et al. |
| 8,160,690 B2 | 4/2012 | Wilfley et al. |
| 8,403,925 B2 | 3/2013 | Miller et al. |
| 8,454,589 B2 | 6/2013 | Deno et al. |
| 8,556,888 B2 | 10/2013 | Nields et al. |
| 9,101,333 B2 | 8/2015 | Schwartz |
| 9,259,290 B2 | 2/2016 | Jenkins et al. |
| 9,271,782 B2 | 3/2016 | Paul et al. |
| 9,283,051 B2 | 3/2016 | Garcia et al. |
| 9,636,164 B2 | 5/2017 | Panescu et al. |
| 9,743,854 B2 | 8/2017 | Stewart et al. |
| 9,757,191 B2 | 9/2017 | Avitall et al. |
| 9,955,946 B2 | 5/2018 | Miller et al. |
| 9,980,653 B2 | 5/2018 | Lichtenstein et al. |
| 10,292,588 B2 | 5/2019 | Ben-Haim |
| 2002/0068931 A1 | 6/2002 | Wong et al. |
| 2003/0074011 A1 | 4/2003 | Gilboa et al. |
| 2003/0220636 A1 | 11/2003 | Bowman et al. |
| 2004/0039278 A1 | 2/2004 | Wacker et al. |
| 2004/0044279 A1 | 3/2004 | Lewin et al. |
| 2004/0097805 A1 | 5/2004 | Verard et al. |
| 2004/0147920 A1 | 7/2004 | Keidar |
| 2004/0176804 A1 | 9/2004 | Palti |
| 2005/0015006 A1 | 1/2005 | Mitschke et al. |
| 2005/0033164 A1 | 2/2005 | Yatsuo et al. |
| 2005/0054913 A1 | 3/2005 | Duerk et al. |
| 2005/0054918 A1 | 3/2005 | Sra |
| 2005/0058328 A1 | 3/2005 | Moreau-Gobard |
| 2005/0245814 A1 | 11/2005 | Anderson et al. |
| 2006/0089552 A1 | 4/2006 | Goldbach |
| 2006/0241401 A1 | 10/2006 | Govari et al. |
| 2007/0043296 A1 | 2/2007 | Schwartz |
| 2007/0049915 A1 | 3/2007 | Haemmerich et al. |
| 2007/0106289 A1 | 5/2007 | O'Sullivan |
| 2007/0167706 A1 | 7/2007 | Boese et al. |
| 2007/0167726 A1 | 7/2007 | Unal et al. |
| 2008/0114235 A1 | 5/2008 | Unal et al. |
| 2008/0118135 A1 | 5/2008 | Averbuch et al. |
| 2008/0125775 A1 | 5/2008 | Morris |
| 2008/0177175 A1 | 7/2008 | Mottola et al. |
| 2008/0183070 A1 | 7/2008 | Unal et al. |
| 2008/0190438 A1 | 8/2008 | Harlev et al. |
| 2008/0208031 A1 | 8/2008 | Kurpad et al. |
| 2008/0221425 A1 | 9/2008 | Olson et al. |
| 2008/0230705 A1 | 9/2008 | Rousso et al. |
| 2008/0275440 A1 | 11/2008 | Kratoska et al. |
| 2008/0275465 A1 | 11/2008 | Paul et al. |
| 2008/0281319 A1 | 11/2008 | Paul et al. |
| 2009/0010519 A1 | 1/2009 | Wakai et al. |
| 2009/0015818 A1 | 1/2009 | Ikeda et al. |
| 2009/0076499 A1 | 3/2009 | Azure |
| 2009/0148012 A1 | 6/2009 | Altmann et al. |
| 2009/0171274 A1 | 7/2009 | Harlev et al. |
| 2009/0221908 A1 | 9/2009 | Glossop |
| 2009/0225077 A1 | 9/2009 | Sudarsky et al. |
| 2009/0262109 A1 | 10/2009 | Markowitz et al. |
| 2009/0275828 A1 | 11/2009 | Shachar et al. |
| 2009/0281566 A1 | 11/2009 | Edwards et al. |
| 2009/0306643 A1 | 12/2009 | Pappone et al. |
| 2010/0063400 A1 | 3/2010 | Hall et al. |
| 2010/0069921 A1 | 3/2010 | Miller et al. |
| 2010/0185087 A1 | 7/2010 | Nields et al. |
| 2010/0217116 A1 | 8/2010 | Eck et al. |
| 2010/0249579 A1 | 9/2010 | Starks |
| 2010/0274239 A1 | 10/2010 | Paul et al. |
| 2010/0283484 A1 | 11/2010 | Cohen et al. |
| 2010/0298826 A1* | 11/2010 | Leo ............... A61B 18/1492 606/41 |
| 2010/0312094 A1 | 12/2010 | Guttman et al. |
| 2010/0312096 A1 | 12/2010 | Guttman et al. |
| 2011/0106221 A1 | 5/2011 | Neal, II et al. |
| 2011/0144524 A1 | 6/2011 | Fish et al. |
| 2011/0230758 A1 | 9/2011 | Eichler |
| 2011/0282186 A1 | 11/2011 | Harlev et al. |
| 2011/0306867 A1 | 12/2011 | Gopinathan et al. |
| 2012/0059249 A1 | 3/2012 | Verard et al. |
| 2012/0078129 A1 | 3/2012 | Bailin |
| 2012/0109115 A1 | 5/2012 | Condie et al. |

(56) References Cited

U.S. PATENT DOCUMENTS

| | | |
|---|---|---|
| 2012/0116210 A1 | 5/2012 | Zino |
| 2012/0123250 A1 | 5/2012 | Pang et al. |
| 2012/0150046 A1 | 6/2012 | Watson et al. |
| 2012/0172724 A1 | 7/2012 | Hill et al. |
| 2012/0173217 A1 | 7/2012 | Heimbecher |
| 2012/0197243 A1 | 8/2012 | Sherman et al. |
| 2012/0238866 A1 | 9/2012 | Wang et al. |
| 2013/0137980 A1 | 5/2013 | Waters et al. |
| 2013/0272593 A1 | 10/2013 | Lee et al. |
| 2013/0310673 A1 | 11/2013 | Govari et al. |
| 2014/0024911 A1 | 1/2014 | Harlev et al. |
| 2014/0088943 A1 | 3/2014 | Trayanova et al. |
| 2014/0187949 A1 | 7/2014 | Zhao et al. |
| 2014/0243641 A1 | 8/2014 | Boveja et al. |
| 2014/0243813 A1 | 8/2014 | Paul et al. |
| 2014/0275991 A1 | 9/2014 | Potter et al. |
| 2014/0330111 A1 | 11/2014 | Lichtenstein et al. |
| 2015/0080762 A1 | 3/2015 | Kassab et al. |
| 2015/0099942 A1 | 4/2015 | Edouard |
| 2015/0141978 A1 | 5/2015 | Subramaniam et al. |
| 2015/0147382 A1 | 6/2015 | Avitall et al. |
| 2015/0223757 A1 | 8/2015 | Werneth et al. |
| 2015/0254422 A1 | 9/2015 | Avisar |
| 2016/0066977 A1 | 3/2016 | Neal, II et al. |
| 2016/0095651 A1 | 4/2016 | Deno et al. |
| 2016/0095653 A1 | 4/2016 | Lambert et al. |
| 2016/0242667 A1 | 8/2016 | Fay et al. |
| 2016/0249989 A1 | 9/2016 | DeVam et al. |
| 2016/0270683 A1 | 9/2016 | Grass et al. |
| 2017/0014181 A1 | 1/2017 | Bar-Tal et al. |
| 2017/0009805 A1 | 4/2017 | Voth |
| 2017/0156792 A1 | 6/2017 | Ziv-Ari et al. |
| 2017/0263021 A1 | 9/2017 | Ben Haim |
| 2017/0281281 A1 | 10/2017 | He et al. |
| 2018/0116751 A1 | 5/2018 | Schwartz et al. |
| 2018/0125575 A1 | 5/2018 | Schwartz et al. |
| 2018/0153437 A1 | 6/2018 | Schwartz et al. |
| 2018/0325597 A1 | 11/2018 | Schwartz et al. |
| 2019/0328458 A1 | 10/2019 | Shmayahu et al. |
| 2019/0336035 A1 | 11/2019 | Dichterman et al. |
| 2019/0340837 A1 | 11/2019 | Shmayahu et al. |
| 2020/0022649 A1 | 1/2020 | Rodriguez et al. |
| 2020/0060757 A1 | 2/2020 | Ben-Haim et al. |
| 2020/0315709 A1 | 10/2020 | Shmayahu et al. |
| 2021/0241542 A1 | 8/2021 | Shmayahu et al. |

FOREIGN PATENT DOCUMENTS

| | | |
|---|---|---|
| EP | 1472975 | 11/2004 |
| EP | 1504713 | 2/2005 |
| EP | 1726268 | 11/2006 |
| EP | 1767166 | 3/2007 |
| EP | 1853162 | 11/2007 |
| EP | 1943974 | 7/2008 |
| EP | 2075763 | 7/2009 |
| EP | 2248480 | 11/2010 |
| EP | 2712543 | 4/2014 |
| EP | 2777584 | 9/2014 |
| HR | P20131208 | 3/2014 |
| JP | 2001-340336 | 12/2001 |
| JP | 2005-199072 | 7/2005 |
| JP | 2009-518130 | 5/2009 |
| JP | 2014-533130 | 12/2014 |
| JP | 2015-503365 | 2/2015 |
| WO | WO 2007/067628 | 6/1997 |
| WO | WO 97/29682 | 8/1997 |
| WO | WO 98/01069 | 1/1998 |
| WO | WO 2007/067628 | 6/2007 |
| WO | WO 2008/097767 | 8/2008 |
| WO | WO 2008/104914 | 9/2008 |
| WO | WO 2010/102794 | 9/2010 |
| WO | WO 2010/129095 | 11/2010 |
| WO | WO 2011/142931 | 11/2011 |
| WO | WO 2012/092016 | 7/2012 |
| WO | WO 2013/052590 | 4/2013 |
| WO | WO 2013/096916 | 6/2013 |
| WO | WO 2013/192598 | 12/2013 |
| WO | WO 2014/118535 | 8/2014 |
| WO | WO 2014/182822 | 11/2014 |
| WO | WO 2016/038499 | 3/2016 |
| WO | WO 2016/088084 | 6/2016 |
| WO | WO 2016/135584 | 9/2016 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |
| WO | WO 2018/078540 | 5/2018 |
| WO | WO 2018/092059 | 5/2018 |
| WO | WO 2018/092062 | 5/2018 |
| WO | WO 2018/092063 | 5/2018 |
| WO | WO 2018/092070 | 5/2018 |
| WO | WO 2018/092071 | 5/2018 |
| WO | WO 2018/130974 | 7/2018 |
| WO | WO 2018/130976 | 7/2018 |
| WO | WO 2018/130981 | 7/2018 |
| WO | WO 2018/134747 | 7/2018 |
| WO | WO 2018/146613 | 8/2018 |
| WO | WO 2018/207128 | 11/2018 |
| WO | WO 2019/034944 | 2/2019 |
| WO | WO 2019/035023 | 2/2019 |
| WO | WO 2019/111180 | 6/2019 |
| WO | WO 2019/215574 | 11/2019 |

OTHER PUBLICATIONS

International Preliminary Report on Patentability dated May 31, 2019 From the International Bureau of WIPO Re. Application No. PCT/IB2017/057175. (9 Pages).
International Preliminary Report on Patentability dated May 31, 2019 From the International Bureau of WIPO Re. Application No. PCT/IB2017/057176. (10 Pages).
Notice of Allowance dated Jan. 8, 2021 From the US Patent and Trademark Office Re. U.S. Appl. No. 16/461,384. (37 pages).
Notice of Allowance dated Mar. 9, 2020 from the US Patent and Trademark Office Re. U.S. Appl. No. 16/349,648. (28 pages).
International Search Report and the Written Opinion dated Jun. 7, 2018 From the International Searching Authority Re. Application No. PCT/IB2018/050289. (16 Pages).
International Search Report and the Written Opinion dated Sep. 25, 2018 From the International Searching Authority Re. Application No. PCT/IB2018/050784. (18 Pages).
Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).
Boston Scientific "Rhythmia™ Mapping System: Rhythmia Disposables Product Information: Intellamap Orion™ High Resolution Mapping Catheter", Boston Scientific, 2 P., Sep. 2015.
Communication Relating to the Results of the Partial International Search dated Aug. 22, 2016 From the International Searching Authority Re. Application No. PCT/IB2016/052686.
Communication Relating to the Results of the Partial International Search dated Aug. 22, 2016 From the International Searching Authority Re. Application No. PCT/IB2016/052688.
Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Preliminary Report on Patentability dated May 9, 2019 From the International Bureau of WIPO Re. Application No. PCT/IB2017/056616. (8 Pages).
International Preliminary Report on Patentability dated Nov. 23, 2017 From the International Bureau of WIPO Re. Application No. PCT/IB2016/052686. (11 Pages).

(56) References Cited

OTHER PUBLICATIONS

International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Preliminary Report on Patentability dated May 31, 2019 From the International Bureau of WIPO Re. Application No. PCT/IB2017/057186. (13 Pages).
International Search Report and the Written Opinion dated Feb. 1, 2018 From the International Searching Authority Re. Application No. PCT/IB2017/056616. (14 Pages).
International Search Report and the Written Opinion dated Jan. 2, 2019 From the International Searching Authority Re. Application No. PCT/IB2018/056158. (16 Pages).
International Search Report and the Written Opinion dated Jan. 3, 2017 From the International Searching Authority Re. Application No. PCT/IB2016/052688. (14 Pages).
International Search Report and the Written Opinion dated May 3, 2018 From the International Searching Authority Re. Application No. PCT/IB2017/057185. (18 Pages).
International Search Report and the Written Opinion dated Jun. 6, 2018 From the International Searching Authority Re. Application No. PCT/IB2018/050201. (24 Pages).
International Search Report and the Written Opinion Dated May 9, 2018 From the International Searching Authority Re. Application No. PCT/IB2018/050192. (16 Pages).
International Search Report and the Written Opinion dated Oct. 12, 2016 From the International Searching Authority Re. Application No. PCT/IB2016/052686.
International Search Report and the Written Opinion dated Aug. 13, 2018 From the International Searching Authority Re. Application No. PCT/IB2018/053258. (15 Pages).
International Search Report and the Written Opinion dated Apr. 14, 2019 From the International Searching Authority Re. Application No. PCT/IB2018/059672. (49 Pages).
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Oct. 21, 2016 From the International Searching Authority Re. Application No. PCT/IB2016/052687. (16 Pages).
International Search Report and the Written Opinion dated Feb. 22, 2018 From the International Searching Authority Re. Application No. PCT/IB2017/057169. (14 Pages).
International Search Report and the Written Opinion dated Feb. 22, 2018 From the International Searching Authority Re. Application No. PCT/IB2017/057175. (15 Pages).
International Search Report and the Written Opinion dated Feb. 22, 2018 From the International Searching Authority Re. Application No. PCT/IB2017/057176. (15 Pages).
International Search Report and the Written Opinion dated Aug. 25, 2016 From the International Searching Authority Re. Application No. PCT/IB2016/052690.
International Search Report and the Written Opinion dated Apr. 30, 2018 From the International Searching Authority Re. Application No. PCT/IB2017/057186. (22 Pages).
International Search Report and the Written Opinion dated Apr. 30, 2018 From the International Searching Authority Re. Application No. PCT/IB2018/050195. (16 Pages).
International Search Report and the Written Opinion dated Nov. 30, 2018 From the International Searching Authority Re. Application No. PCT/IB2018/055344. (15 Pages).
Invitation to Pay Additional Fees and Communication Related to the Results of the Partial International Search and the Provisional Opinion dated Feb. 22, 2018 From the International Searching Authority Re. Application No. PCT/IB2017/057186. (12 Pages).
Invitation to Pay Additional Fees, Communication Relating to the Results of the Partial International Search and the Provisional Opinion dated Mar. 5, 2018 From the International Searching Authority Re. Application No. PCT/IB2017/057185. (13 Pages).
Invitation to Pay Additional Fees, Communication Relating to the Results of the Partial International Search and the Provisional Opinion dated Apr. 25, 2018 From the International Searching Authority Re. Application No. PCT/IB2018/050201. (14 Pages).
Notice Of Allowance dated Dec. 26, 2018 From the US Patent and Trademark Office Re. U.S. Appl. No. 15/572,815. (8 pages).
Official Action dated Aug. 30, 2018 From the US Patent and Trademark Office Re. U.S. Appl. No. 15/572,815. (22 pages).
Ahn et al. "Height-Based Deformation and Ray Supersampling for Colon Unfolding", ICAT'06 Proceedings of the 16th International Conference on Advances in Artificial Reality and Tele-Existence, Lecture Notes in Computer Science, XP047402101, Hangzhou, China, Nov. 29-Dec. 1, 2006, p. 1098-1107, Nov. 29, 2006. Sections 3.1, 3.3, 5, Figs.2, 4, 5.
Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Bartroli et al. "Nonlinear Virtual Colon Unfolding", Proceedings of the IEEE Conference on Visualization '01, VIS '01, XP031385694, San Diego, CA, USA, Oct. 21-26, 2001, p. 411-420, Oct. 21, 2001. Sections 4, 4.1, 4.2, 5.1, 7, Figs.l, 7a, 7b, 10.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Canpolat et al. "Relationship Between Vitamin D Level and Left Atrial Fibrosis in Patients With Lone Paroxysmal Atrial Fibrillation Undergoing Cryoballoon-Based Catheter Ablation", Journal of Cardiology, 6991): 16-23, Published Online Aug. 21, 2016.
Caspi et al. "Modeling of Arrhythmogenic Right Ventricular Cardiomyopathy With Human Induced Pluripotent Stem Cells", Circulation: Cardiovscular Genetics, 6(6): 557-568, Published Online Nov. 7, 2013.
Cerit et al. "Association of Pre-Ablation Level of Vitamin D With Atrial Fibrillation Recurrence After Catheter Ablation", Europace, 19(9): 1586, Sep. 1, 2017.
Chierchia et al. "An Initial Clinical Experience With A Novel Microwave Radiometry Sensing Technology Used in Irrigated RF Ablation for Flutter", Academic Hospital Brussels, Belgium, 1 P. Jan. 1, 2011.
Crospon "Esophageal Treatment by Esoflip®", Crospon, Product Sheet, 4 P., 2017.
Crospon "Flip® Technology", Crospon, Product Sheet, 6 P., 2017.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.

(56) References Cited

OTHER PUBLICATIONS

Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets Identified by Pre-Ablation Mapping with the AcQMap System: Update on the UNCOVER-AF Trial," EP Lab Digest, 17(5), May 2017, 5 pages.
Hilbert et al. "An Integrative Approach to Slow Pathway Modulation in AVNRT Using A Novel Ultra High-Density Electroanatomical Mapping System", Clinical Research in Cardiology, XP035518036, 104(8): 697-699, Published Online Mar. 31, 2015.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA, May 9-12, 2012, Session: Role of Autonomies in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10, 2012.
Jiang et al. "Association of Pre-Ablation Level of Potential Blood Markers With Atrial Fibrillation Recurrence After Catheter Ablation: A Meta-Analysis", Europace, 19(3): 392-400, Mar. 1, 2017.
Karim et al. "Surface Flattening of the Human Left Atrium and Proof-of-Concept Clinical Applications", Computerized Medical Imaging and Graphics, 38(4): 251-266, Jun. 2014.
Lardo et al. "Visualization and Temporal/Spatial Characterization of Cardiac Radio frequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
McDowell et al. "Virtual Electrophysiological Study of Atrial Fibrillation in Fibrotic Remodeling", PLOS ONE, 10(2): e117110-1-e117110-16, Published Online Feb. 18, 2015.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Ranjan et al. "Gaps in the Ablation Line as A Potential Cause of Recovery From Electrical Isolation and Their Visualization Using MRI", Circulation: Arrhythmia and Electrophysiology, XP055452459, 4(3): 279-286, Published Online Apr. 14, 2011.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.

Shoemaker et al. "Common Genetic Variants and Response to Atrial Fibrillation Ablation", Circulation: Arrhythmia and Electrophysiology, 8(2): 296-302, Published Online Feb. 14, 2015.
St. Jude Medical "Cardiac Mapping System / ECG. NSite™ NavX™", St. Jude Medical, Products Sheet, 22 P., 2017.
Ueberham et al. "Genetic ACE I/D Polymorphism and Recurrence of Atrial Fibrillation After Catheter Ablation", Circulation: Arrhythmia and Electrophysiology, 6(4): 732-737, Published Online Jul. 22, 2013.
Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.
Wang et al. "Association of the Angiotensinogen M235T Polymorphism With Recurrence After Catheter Ablation of Acquired Atrial Fibrillation", Journal of the Renin-Angiotensin-Aldosterone System, 16(4): 888-897, Published Online Aug. 3, 2015.
Wang et al. "Colon Unravelinp Based on Electrical Field: Recent Progress and Further Work", Proceedings of the SPIE 3660 Medical Imaging '99: Physiology and Function From Multidimensional Images, San Diego, CA, USA, Feb. 1999, XP055479173, 3660: 125-133, May 20, 1999. Abstract, Sections 1, 2.2, 2.3, Figs.2, 3.
Wang et al. "Microwave Radiometric Thermoetry and Its Potential Applicability to Ablative Therapy", Journal of Interventional Cardiac Electrophysiology, 4(1): 295-300, Feb. 2000.
Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
Communication Pursuant to Article 94(3) EPC dated Sep. 4, 2020 From the European Patent Office Re. Application No. 16725589.2. (8 Pages).
Communication Pursuant to Article 94(3) EPC dated Sep. 25, 2020 From the European Patent Office Re. Application No. 16726181.7. (5 Pages).
Decision of Refusal dated Oct. 20, 2020 From the Japan Patent Office Re. Application No. 2017-558704 and Its Translation Into English. (6 Pages).
Final Official Action dated Jul. 1, 2020 from the US Patent and Trademark Office Re. U.S. Appl. No. 15/570,341. (24 pages).
Final Official Action dated Jun. 22, 2020 from the US Patent and Trademark Office Re. U.S. Appl. No. 15/573,491. (14 pages).
International Preliminary Report on Patentability dated Jun. 18, 2020 From the International Bureau of WIPO Re. Application No. PCT/IB2018/059672. (8 Pages).
International Preliminary Report on Patentability dated Nov. 21, 2019 From the International Bureau of WIPO Re. Application No. PCT/IB2018/053258. (8 Pages).
International Preliminary Report on Patentability dated Aug. 22, 2019 From the International Bureau of WIPO Re. Application No. PCT/IB2018/050784. (11 Pages).
International Preliminary Report on Patentability dated Jul. 25, 2019 From the International Bureau of WIPO Re. Application No. PCT/IB2018/050192. (8 Pages).
International Preliminary Report on Patentability dated Jul. 25, 2019 From the International Bureau of WIPO Re. Application No. PCT/IB2018/050195. (9 Pages).
International Preliminary Report on Patentability dated May 31, 2019 From the International Burau of WIPO Re. Application No. PCT/IB2017/057185. (11 Pages).
Interview Summary dated Dec. 15, 2020 from the US Patent and Trademark Office Re. U.S. Appl. No. 15/570,341. (4 pages).
Interview Summary dated Sep. 29, 2020 from the US Patent and Trademark Office Re. U.S. Appl. No. 15/573,491. (3 pages).
Notice of Allowance dated Oct. 22, 2020 From the US Patent and Trademark Office Re. U.S. Appl. No. 15/573,491. (6 Pages).
Notice of Allowance dated Feb. 24, 2021 From the US Patent and Trademark Office Re. U.S. Appl. No. 15/570,341. (8 Pages).
Notice of Allowance dated Sep. 4, 2020 from the US Patent and Trademark Office Re. U.S. Appl. No. 15/573,493. (14 pages).

(56) References Cited

OTHER PUBLICATIONS

Notice of Reasons for Refusal dated Mar. 3, 2020 From the Japan Patent Office Re. Application No. 2017-558704 and Its Translation Into English. (14 Pages).
Notice of Reasons for Refusal dated Apr. 21, 2020 From the Japan Patent Office Re. Application No. 2017-558702 and Its Translation Into English. (16 Pages).
Official Action dated Mar. 5, 2020 From the US Patent and Trademark Office Re. U.S. Appl. No. 15/573,493. (21 pages).
Official Action dated Feb. 6, 2020 From the US Patent and Trademark Office Re. U.S. Appl. No. 15/570,341. (33 pages).
Official Action dated Jan. 8, 2020 From the US Patent and Trademark Office Re. U.S. Appl. No. 15/573,491. (20 pages).
Restriction Official Action dated Nov. 19, 2019 From the US Patent and Trademark Office Re. U.S. Appl. No. 15/573,493. (6 pages).
Anselmino et al. "A New Electrophysiology Era: Zero Fluoroscopy", Journal of Cardiovascular Medicine, 14(3): 221-227, Mar. 2013.
Avitall et al. "Novel Dye-Less and Fluoro-Less Approach to Cryoballoon Pulmonary Vein Occlusion Assessment", Heart Rhythm, 14(8): 1241-1246, Aug. 2017.
Bulava et al. "Catheter Ablation of Atrial Fibrillation Using Zero-Fluoroscopy Technique: A Randomized Trial", PACE: Pacing and Clinical Electricophysiology, 38(7): 797-806, Published Online Apr. 16, 2015.
Giaccardi et al. "Near-Zero X-Ray in Arrhythmia Ablation Using A 3-Dimensional Electroanatomic Mapping System: A Multicenter Experience", Heart Rhythm, 13(1): 150-156, Published Online Sep. 1, 2015.
Hou et al. "Fluoroscopy-Free Electrophysiology Study Using 3D Electroanatomic Mapping System: A Case Report and Review of Literature", Journal of Cardiology & Clinical Research, 5(3): 1100-1-1100-4, Mar. 9, 2017.
Koruth et al. "Tissue Temperature Sensing During Irrigated Radiofrequency Ablation: A Novel Strategy to Predict Steam Pops", Heart Rhythm, 33rd Annual Scientific Sessions, Boston, MA, USA, May 9-12, 2012, Presentation Abstract, # AB12-02, May 10, 2012.
Luani et al. "Zero-Fluoroscopy Cryothermal Ablation of Atrioventricular Nodal Reentry Tachycardia Guided by Endovascular and Endocardial Cetheter Visualization Using Intracardia Echocardiography (Ice&ICE Trial)", Journal of Cardiovascular Electrophysiology, 29(1): 160-166, Published Online Oct. 26, 2017.
Macias et al. "A Zero-Fluoroscopy Approach to Cavotricuspid Isthmus Catheter Ablation: Comparative Analysis of Two Electroanatomical Mapping Systems", PACE: Pacing and Clinical Electrophysiology, 37(8): 1029-1037, Published Online Mar. 13, 2014.
O'Brien et al. "Fluoroscopy-Free AF Ablation Using Transesophageal Echocardiography and Electroanatomical Mapping Technology", Journal of Interventional Cardiac Electrophysiology, 50(3): 235-244, Published Online Nov. 14, 2017.
Pinkstone "Needles With Built-In Cameras the Same Width as A Human Hair Capture Ultrasound Images INSIDE Patients to Help Surgeons Perform Keyhole Surgery", MailOnline, 27 P., Dec. 1, 2017.
Sommer et al. "Safety Profile of Near-Zero Fluoroscopy Atrial Fibrillation Ablation With Non-Fluoroscopic Catheter Visualization: Experience From 1000 Consecutive Procedures", Europace, 20(12): 1952-1958, Published Online Jan. 16, 2016.
Sulkin et al. "Novel Measure of Local Impedance Predicts Catheter-Tissue Contact and Lesion Formation", Circulation: Arrhythmia and Electrophysiology, 11(4): e005831-1-e005831-21, Apr. 2018.
Wang et al. "Ablation of Idiopathic Ventricular Arrhythmia Using Zero-Fluoroscopy Approach With Equivalent Efficacy and Less Fatigue—A Multicenter Comparative Study", Medicine, 96(6): e6080-1-e6080-7, Feb. 2017.
Wannagat et al. "Implemenation of A Near-Zero Fluoroscopy Approach in Interventional Electrophysiology: Impact of Operator Experience", Journal of Interventional Cardiac Electrophysiology, 51(3): 215-220, Published Online Feb. 19, 2018.
Yang et al. "Meta-Analysis of Zero or Near-Zero Fluoroscopy Use During Ablation of Cardiac Arrhythmias", The American Journal of Cardiology, 118(10): 1511-1518, Published Online Aug. 24, 2016.

\* cited by examiner
† cited by third party

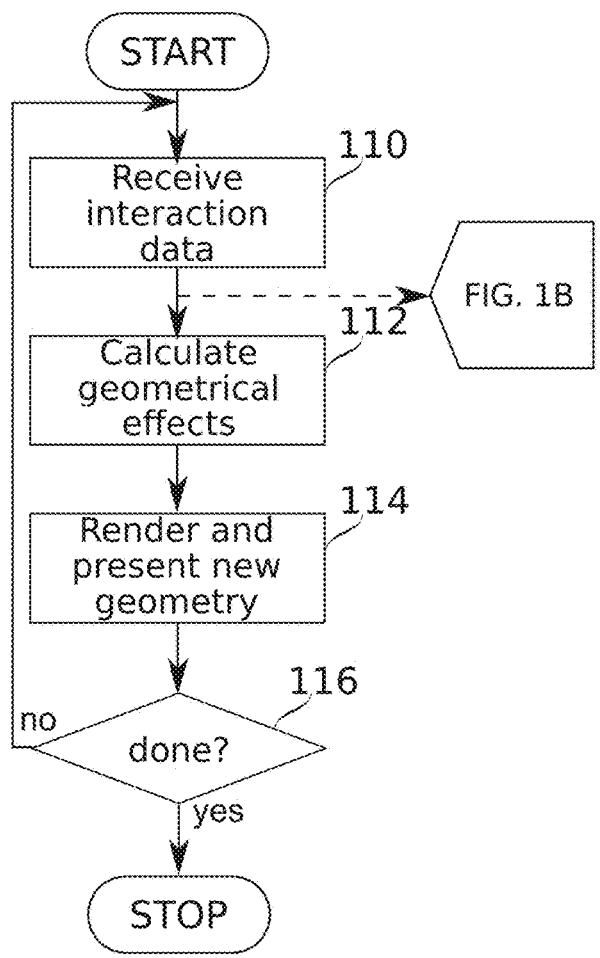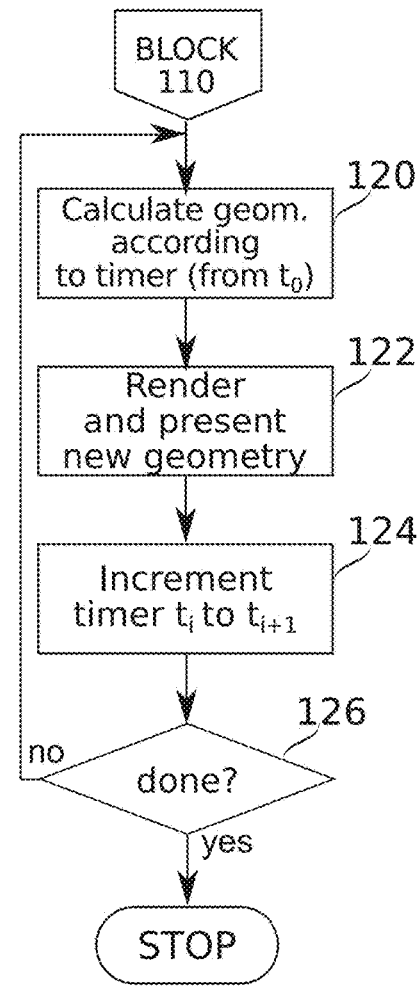
FIG. 1A
FIG. 1B

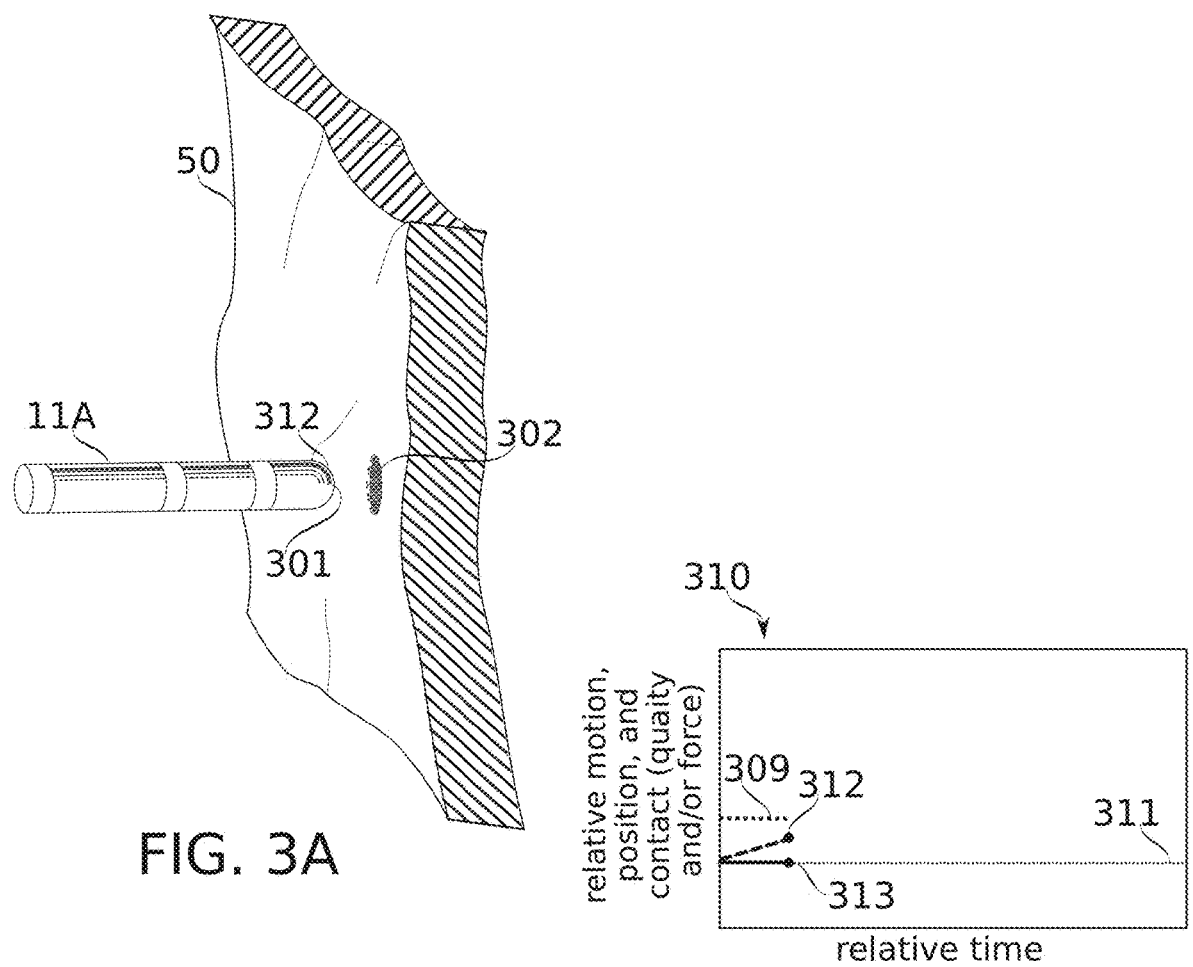
FIG. 3A
FIG. 3B
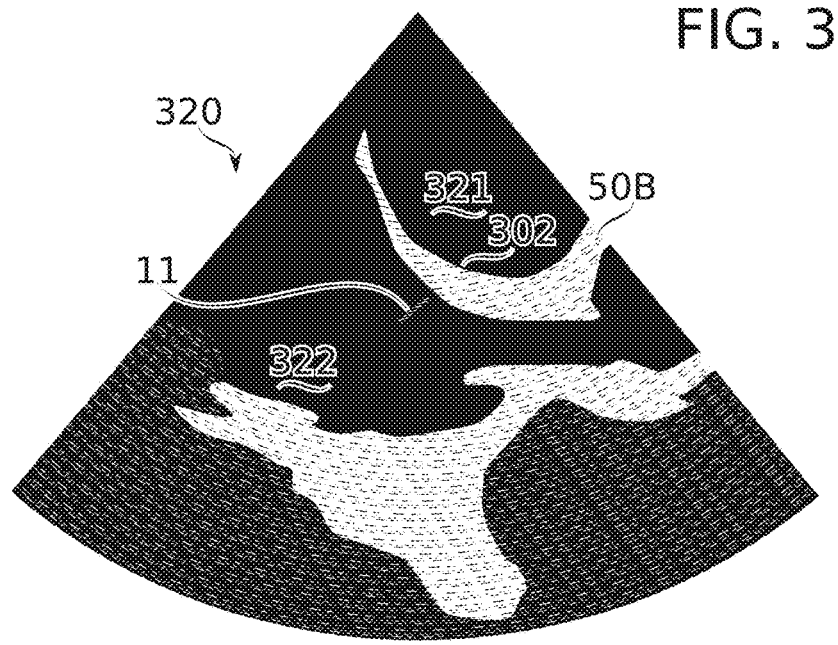
FIG. 3C

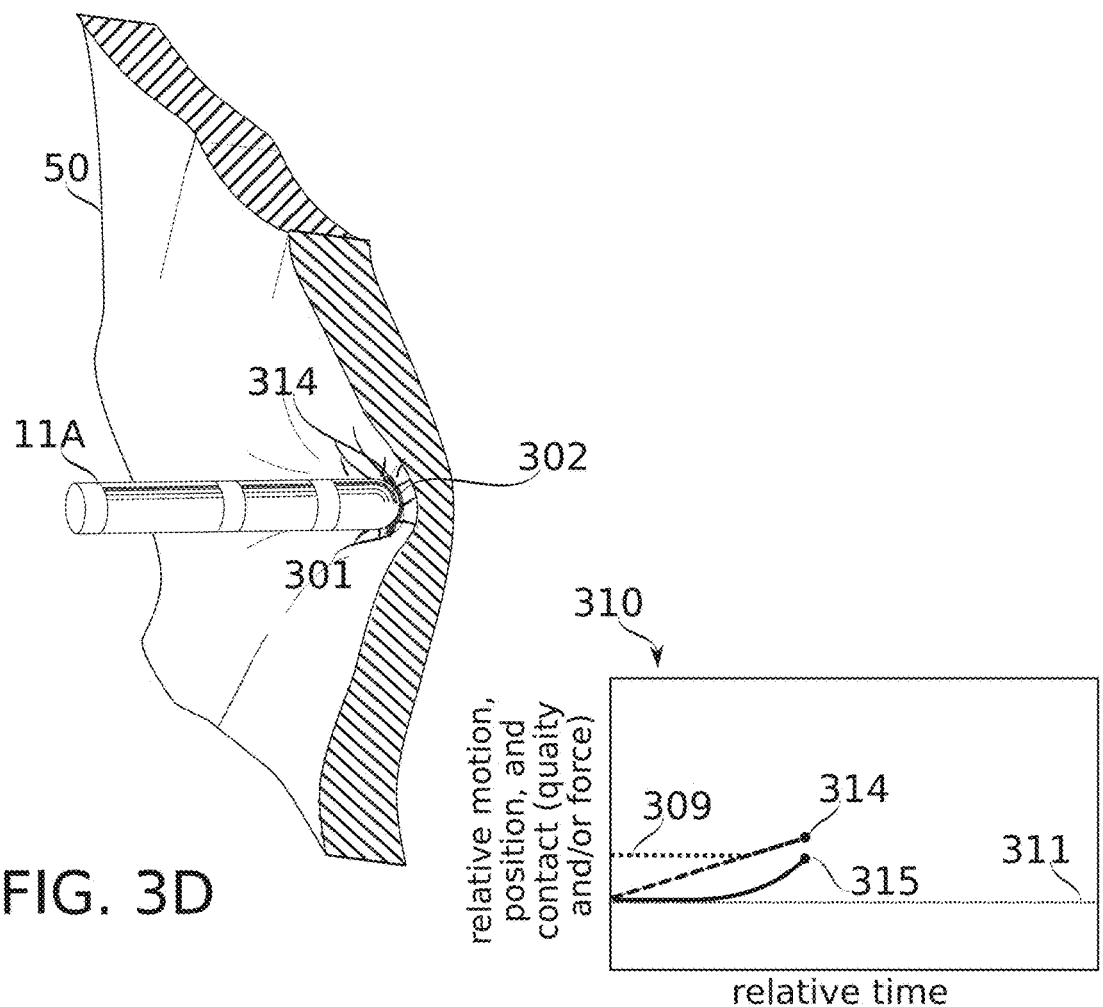
FIG. 3D
FIG. 3E
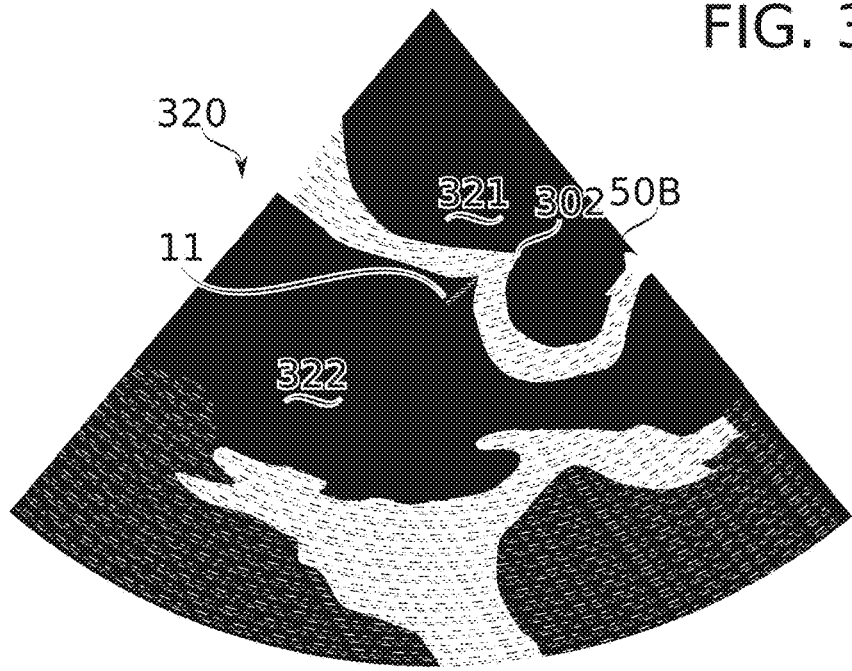
FIG. 3F

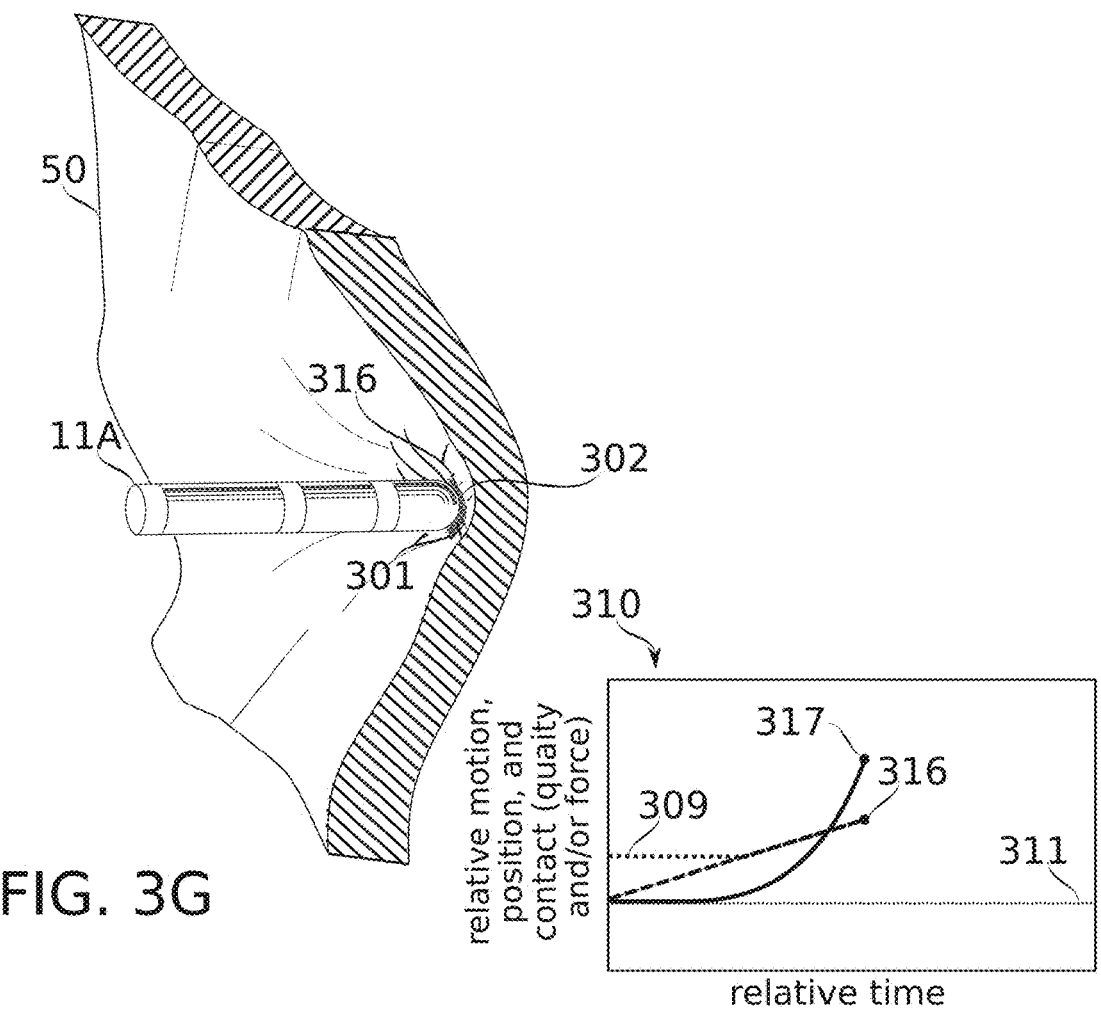
FIG. 3G
FIG. 3H
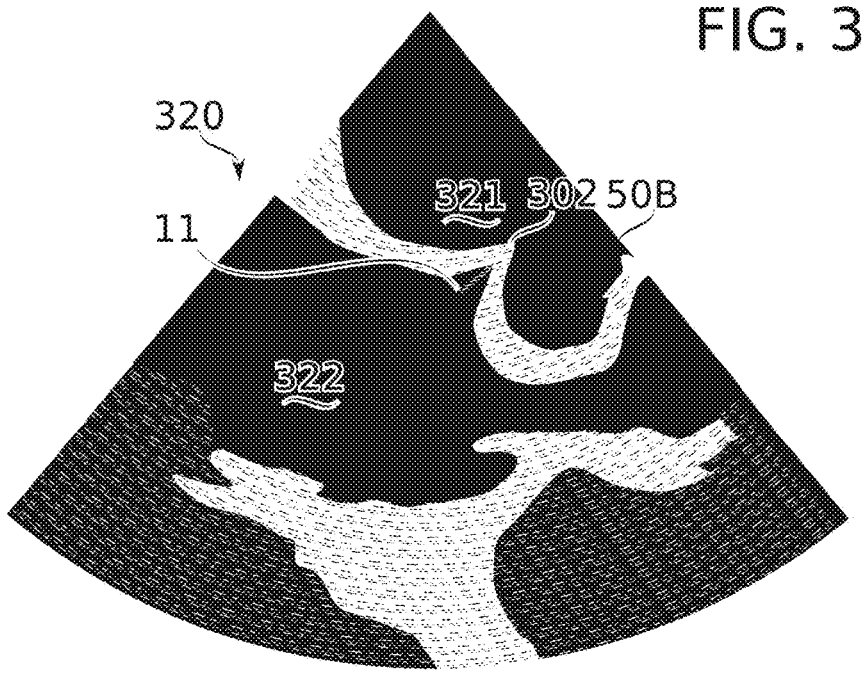
FIG. 3I

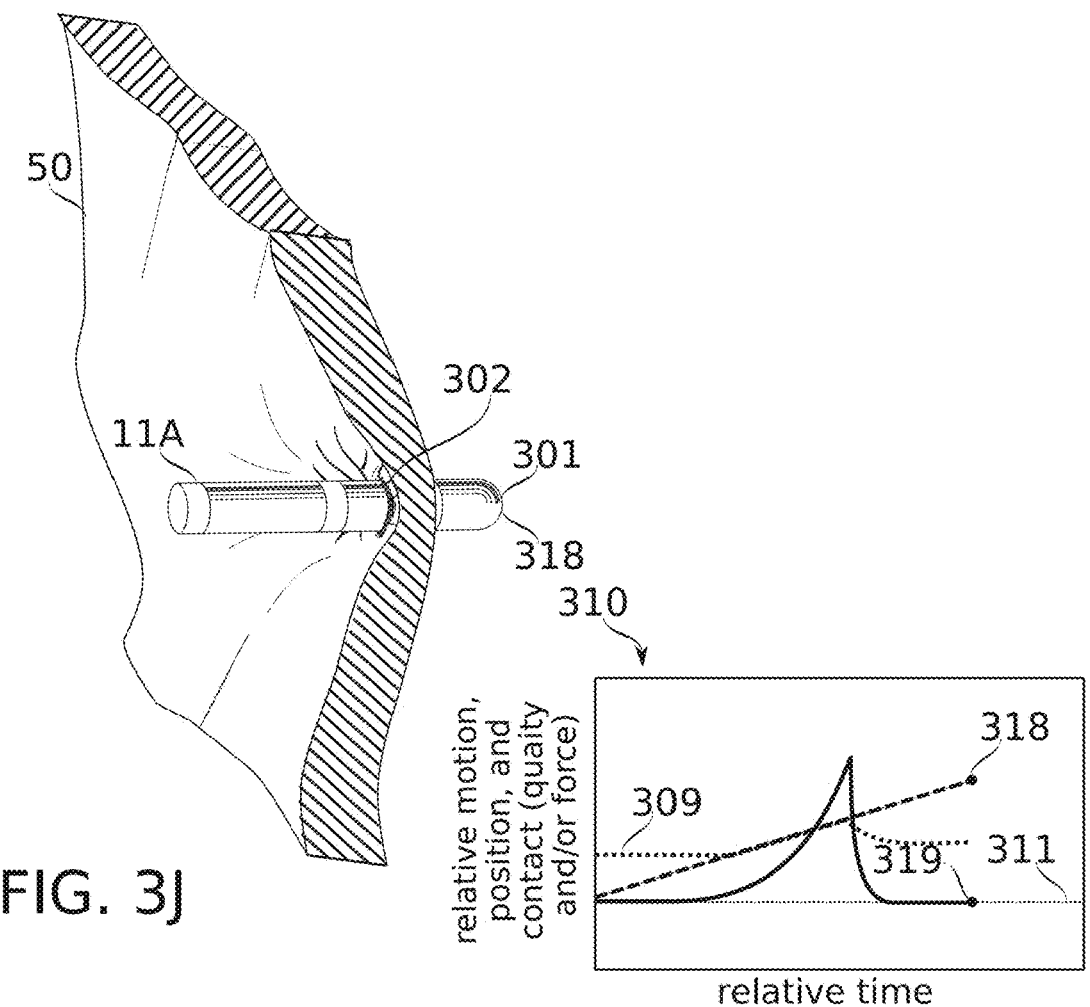
FIG. 3J
FIG. 3K
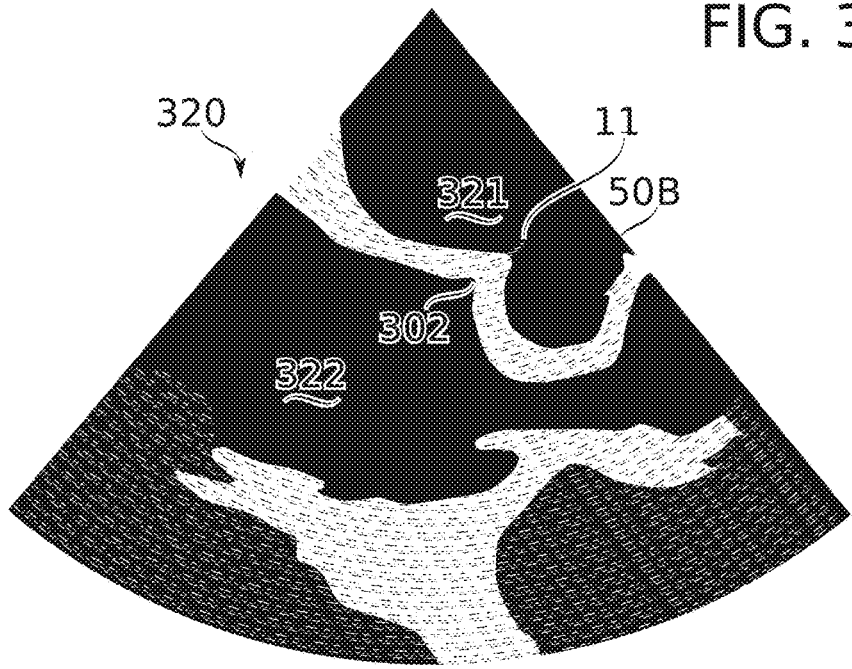
FIG. 3L

REAL-TIME DISPLAY OF TISSUE DEFORMATION BY INTERACTIONS WITH AN INTRA-BODY PROBE

RELATED APPLICATIONS

This application is a National Phase of PCT Patent Application No. PCT/IB2017/057175 having International filing date of Nov. 16, 2017, which claims the benefit of priority under 35 USC § 119(e) of U.S. Provisional Patent Application Nos. 62/422,705, 62/422,708 and 62/422,713, all filed on Nov. 16, 2016. The contents of the above applications are all incorporated by reference as if fully set forth herein in their entirety.

FIELD AND BACKGROUND OF THE INVENTION

The present invention, in some embodiments thereof, relates to the field of medical procedures using intrabody probes navigable within intrabody spaces, and more particularly, to presentation of procedure data dynamically acquired during the course of a catheter procedure.

Graphical game engines currently available comprise suites of software-implemented capabilities supporting the dynamic display and updating of simulated three-dimensional scenes. Typically, game engines include API calls supporting the creation and modification of a variety of scene objects (chiefly terrain, various types of physical objects, camera viewpoints, and lighting), a visual rendering pipeline, and optionally further services assisting tasks such as coding, animating, and/or debugging. User inputs are accepted from various user interface devices (including pointer devices, keyboards, game controllers, motion sensors, touch screens and the like) and converted into events in the simulated environment. Well-known game engines include the Unreal® and Unity® graphical game engines (www(dot)unrealengine(dot)com; www(dot)unity3d(dot) com). The rendering pipelines of modern game engines typically include facilities for creating realistic-looking visualizations of scene elements, based on properties assigned to instantiations of data objects representing those scene elements.

Several medical procedures in cardiology and other medical fields comprise the use of catheters to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field-guided position sensing systems. Refinements to techniques for registration of previously imaged (for example, by CT and/or MRI) anatomical features of a patient to electromagnetic field-sensed catheter position are a subject of ongoing research and development, for example as described in International Patent Application No. IB2016/052687 to Schwartz et al. filed May 11, 2016; and International Patent Application No. IB2016/052692 to Schwartz et al. filed May 11, 2016. Intrabody sensing from catheter probes to determine information about, for example, tissue contact and/or lesion assessment, has also been described (e.g., International Patent Application No. PCT IB2016/052690 to Schwartz et al. filed May 11, 2016; and International Patent Application No. IB2016/052686 to Schwartz et al. filed May 11, 2016).

SUMMARY OF THE INVENTION

There is provided, in accordance with some embodiments of the present disclosure, a method of visually displaying effects of a medical procedure, comprising: receiving interaction data from an intrabody probe indicating touching contacts between the intrabody probe and a body tissue region, wherein the interaction data at least associate the contacts to contacted positions of the body tissue region; adjusting geometrical rendering data representing a shape of the body tissue region to obtain adjusted geometrical rendering data, wherein the adjusting is based on an indication in the interaction data of a change in the shape of the body tissue region due to the contacting; rendering the adjusted geometrical rendering data to a rendered image; and displaying the rendered image.

In some embodiments, the intrabody probe is a catheter probe.

In some embodiments, the geometrical rendering data are adjusted as a function of time relative to a time of occurrence of at least one of the indicated contacts.

In some embodiments, the receiving, the adjusting, and the displaying are performed iteratively for a sequence of contacts for which interaction data is received.

In some embodiments, the adjusting is at a frame rate of 10 frames per second or more.

In some embodiments, the rendering and the displaying are at a frame rate of 10 frames per second or more.

In some embodiments, the geometrical rendering data include a representation of 3-D surface positions and a representation of surface orientations; wherein the two representations each correspond to a same portion of the shape of the body tissue region; and wherein the adjusting comprises adjusting the surface orientation representation to change a geometrical appearance in the rendering.

In some embodiments, the representation of surface orientation is adjusted separately from the representation of 3-D surface positions.

In some embodiments, the extent and degree of the adjusting model a change in a thickness of the body tissue region.

In some embodiments, the interaction data describe an exchange of energy between the intrabody probe and the body tissue region by a mechanism other than contact pressure.

In some embodiments, the adjusting comprises updating the geometrical rendering data based on a history of interaction data describing the exchange of energy.

In some embodiments, the exchange of energy comprises operation of an ablation modality.

In some embodiments, the updating changes an indication of lesion extent in the geometrical rendering data based on the history of interaction data describing the exchange of energy by operation of the ablation modality.

In some embodiments, the updating comprises adjusting the geometrical rendering data to indicate a change in mechanical tissue properties, based on the history of interaction data describing the exchange of energy.

In some embodiments, the ablation energy exchanged between the intrabody probe and the body tissue region comprises at least one of the group consisting of: radio frequency ablation, cryoablation, microwave ablation, laser ablation, irreversible electroporation, substance injection ablation, and high-intensity focused ultrasound ablation.

In some embodiments, the updating comprises adjusting the geometrical rendering data to indicate a change in tissue thickness, based on the history of interaction data describing the exchange of energy.

In some embodiments, effects of the history of interaction data describing the exchange of energy are determined from modelling of thermal effects of the exchange of energy on the body tissue region.

In some embodiments, the modelling of thermal effects accounts for local tissue region properties affecting transfer of thermal energy between the intrabody probe and the body tissue region.

In some embodiments, the adjusting is as a function of time relative to a time of occurrence of at least one of the indicated contacts, and comprises adjusting the geometrical rendering data to indicate gradual development of a change in geometry of the body tissue region as a result of the contacts.

In some embodiments, the gradually developed change in geometry indicates a developing state of edema.

In some embodiments, the method comprises geometrically distorting the rendering of the geometrical rendering data into a swollen appearance, to an extent based on the indicated development of the state of edema.

In some embodiments, the contacts comprise mechanical contacts, and the gradual development of a change in geometry indicates swelling of the body tissue region in response to tissue irritation by the mechanical contacts.

In some embodiments, the contacts comprise an exchange of energy between the intrabody probe and the body tissue region by a mechanism other than contact pressure.

In some embodiments, the interaction data indicate a contact force between the intrabody probe and the body tissue region.

In some embodiments, the interaction data indicate a contact quality between the intrabody probe and the body tissue region.

In some embodiments, the interaction data indicate a geometrical distortion introduced by touching contact between the intrabody probe and the body tissue region.

In some embodiments, the adjusting comprises geometrically distorting the rendering of the geometrical rendering data at a region of touching contact to an extent based on the interaction data.

In some embodiments, the geometrically distorting the rendering of the geometrical rendering data includes geometrically distorting a portion of the geometrical rendering data which is not geometrically corresponding to the portion of the body tissue region from which the interaction data were obtained.

In some embodiments, the interaction data comprises a 2-D image including a cross-sectional view of the body tissue region, and the distorted portion of the geometrical rendering extends out of a plane in the geometrical rendering data corresponding to the plane of the cross-sectional view.

In some embodiments, the interaction data describes injection of a substance from the intrabody probe to the body tissue region, and the adjusting comprises changing a thickness of tissue in the body tissue region, corresponding to an effect of the injection of the substance.

In some embodiments, the rendering includes a view of the intrabody probe.

In some embodiments, the rendering is rendered from a viewpoint at least partially defined by a measured position of the intrabody probe relative to a surface of the body tissue region.

In some embodiments, the measured position includes a measured orientation of the intrabody probe.

In some embodiments, the intrabody probe contacts a lumenal surface of the body tissue region.

In some embodiments, the intrabody probe contacts an external surface of an organ comprising the body tissue region.

In some embodiments, the body tissue region comprises a tissue of at least one organ of the group consisting of the heart, vasculature, stomach, intestines, liver and kidney.

In some embodiments, the method further comprises assigning material appearance properties across an extent of the geometrical rendering data, based on the interaction data; and wherein the displaying of the rendered image uses the assigned material appearance properties.

In some embodiments, the rendering comprises a rendering in cross-section of the body tissue region.

In some embodiments, the extent and degree of the adjusting simulate stretching of the body tissue region.

In some embodiments, the geometrical rendering data represent a shape of a body tissue region comprising a heart chamber; and wherein the adjusting comprises adjusting a size of the heart chamber, based on the current heart rate data.

In some embodiments, the adjusting a size of the heart chamber comprises adjusting a size of a lumen of the heart chamber, based on the current heart rate data.

In some embodiments, the adjusting a size of the heart chamber comprises adjusting a thickness of a wall of the heart chamber, based on the current heart rate data.

In some embodiments, the adjusting geometrical rendering data comprises adjusting a position of the intrabody probe in the geometrical rendering data relative to a wall of the heart chamber, based on the current heart rate data.

There is provided, in accordance with some embodiments of the present disclosure, a system for visually displaying effects of interactions between an intrabody probe and a body tissue region, the system comprising computer circuitry configured to: receive interaction data indicating the interactions, and associated to positions on a surface of the body tissue region; adjust geometrical rendering data representing a shape of the body tissue region to obtain adjusted geometric rendering data, wherein the adjusting is based on an indication in the interaction data of a change in the shape of the body tissue region; render the adjusted geometrical rendering data to a rendered image; and present the rendered image.

In some embodiments, the rendering is performed using a graphical game engine, and the interaction data include sensed positions of the intrabody probe.

In some embodiments, the interaction data include probe-sensed characteristics of tissue in the vicinity of the intrabody probe.

In some embodiments, the interaction data includes operational data describing operation of the intrabody probe to treat tissue.

There is provided, in accordance with some embodiments of the present disclosure, a method of visually displaying a medical procedure, comprising: receiving position data indicating the position of an intracardial probe within a heart; receiving heart rate data for the heart; adjusting geometrical rendering data representing a shape of the heart and a shape and position of the intracardial probe to obtain adjusted geometric rendering data; wherein the adjusting is based on the heart rate data to maintain an accuracy of positioning of the intracardial probe relative to the heart as average size of the heart changes as a function of a heart rate; rendering the adjusted geometrical rendering data to a rendered image; and displaying the rendered image.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 1A is a schematic flowchart illustrating the calculation and display of an image of a scene comprising simulated tissue having a geometry and/or geometrical appearance dynamically linked to interactions of the tissue with a catheter probe, according to some embodiments of the present disclosure;

FIG. 1B is a schematic flowchart illustrating the calculation and display of a geometry and/or geometrical appearance dynamically changing over time as a result of prior interaction of the tissue with a catheter probe, according to some embodiments of the present disclosure.

FIGS. 3A, 3D, 3G, and 3J schematically represent a sequence of rendered views of a catheter probe passing through a tissue wall portion, according to some embodiments of the present disclosure;

FIGS. 3B, 3E, 3H, and 3K schematically represent a graph of position versus time and measured contact versus time for the catheter probe of FIGS. 3A, 3D, 3G, and 3J, according to some embodiments of the present disclosure;

FIGS. 3C, 3F, 3I, and 3L schematically represent an ultrasound image at a cross-section of a heart at the atrial level, and corresponding to the sequence of FIGS. 3A, 3D, 3G, and 3J, according to some embodiments of the present disclosure;

DESCRIPTION OF SPECIFIC EMBODIMENTS OF THE INVENTION

Figure 2A:
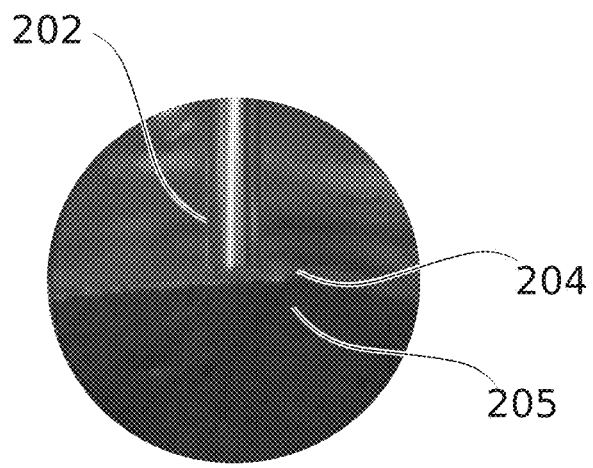
FIGS. 2A-2E illustrate a-D rendered display for indicating lesioning status to a user, according to some exemplary embodiments of the present disclosure.

The present invention, in some embodiments thereof, relates to the field of medical procedures using intrabody probes navigable within intrabody spaces, and more particularly, to presentation of procedure data dynamically acquired during the course of a catheter procedure.

Overview

An aspect of some embodiments of the current invention relates to the motion frame-rate, real-time display of geometrical effects on a simulation scene comprising simulated tissue, wherein the geometrical effects comprise changes to a geometrical representation of one or more elements in the scene, and wherein the changes are made based on ongoing and/or intermittent measurements of interactions between a catheter probe and the actual tissue being simulated.

Herein, "geometrical effects" optionally comprise one or both of changes to the 3-D position of simulated elements, and changes to the geometrical appearance of simulated elements. Geometrical appearance, as distinct from 3-D position, comprises geometrical that can give a relatively raised, indented, smoothed, irregular, blurred, focused, closer, further, shaded, and/or unshaded appearance to a portion of a surface, without affecting 3-D coordinates of the surface itself. Geometrical appearance optionally comprises features implemented at least in part by computational methods—for example, normal mapping, depth mapping, and/or shadow mapping.

In some embodiments, a software environment specialized for interactive visual simulations (for example a 3-D graphical game engine such as the Unreal® and/or Unity® graphical game engines) is used as a basis for implementing a simulation of a scene comprising simulated tissue (herein, such a scene is referred to as a simulation scene). For rendering images by the game engine's graphics pipeline, geometrical rendering data are optionally supplemented with one or more material appearance properties (preferably a plurality of such properties) that describe how virtual materials such as simulated tissue interact with simulated optical laws and lighting conditions to generate images for display. The geometrical rendering data optionally comprises a geometrical representation of a scene including tissue. In some embodiments, the rendering is implemented, by a rendering pipeline of the graphical game engine.

It should be understood that one or more capabilities used by some embodiments of the present invention and described as implemented by a game engine are optionally provided by alternative implementations not packaged in a game engine distribution, including: use of customized software, firmware and/or hardware; and/or use of separately distributed software libraries. The term "game engine" as used herein should be understood to encompass computer-implemented collections of such typical game engine capabilities as may be used by some embodiments of the present invention (examples of which are described herein), whether or not they have been packaged into a game engine distribution.

As used herein, the term "rendering" refers to the process of generating an image from a 2-D or 3-D model or models by means of one or more computer programs. The model may contain object parameter definitions and/or data structures; for example, geometry, viewpoint, texture, lighting, and/or shading information as a description of the virtual model. The data contained in the model may be passed to a rendering program to be processed and output to a digital image or raster graphics image file. The processing comprises one or more processing stages referred to collectively as a "pipeline", and carried out by the software and hardware of a rendering device. In some embodiments, the rendering device includes one or more of a general purpose CPU and graphics hardware specialized for use within a rendering pipeline.

Figure 6:
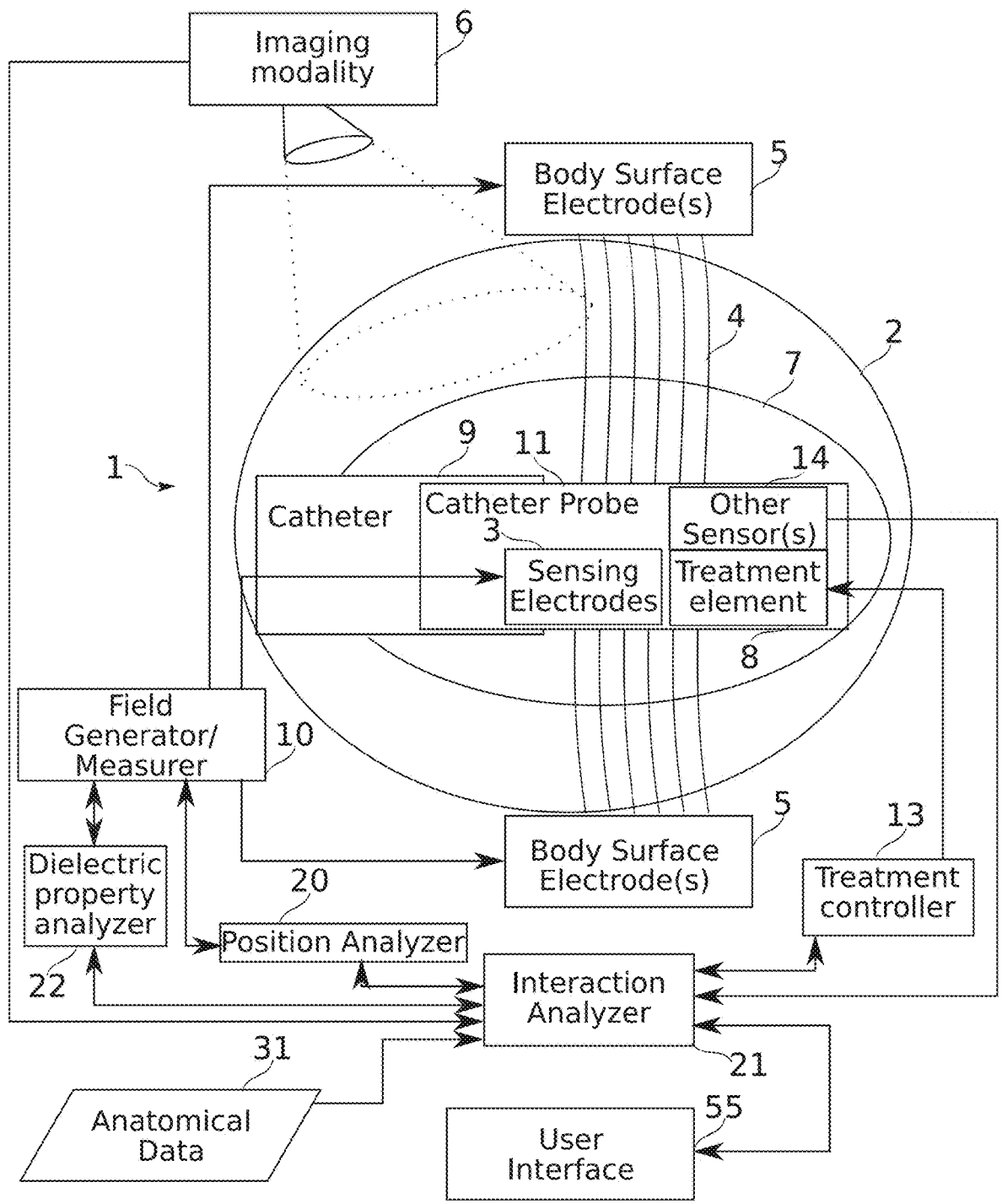
FIG. 6 is a schematic representation of a system configured for display of interactions between a catheter probe and a body tissue region, and/or their effects, according to some embodiments of the present disclosure.
Figure 7:
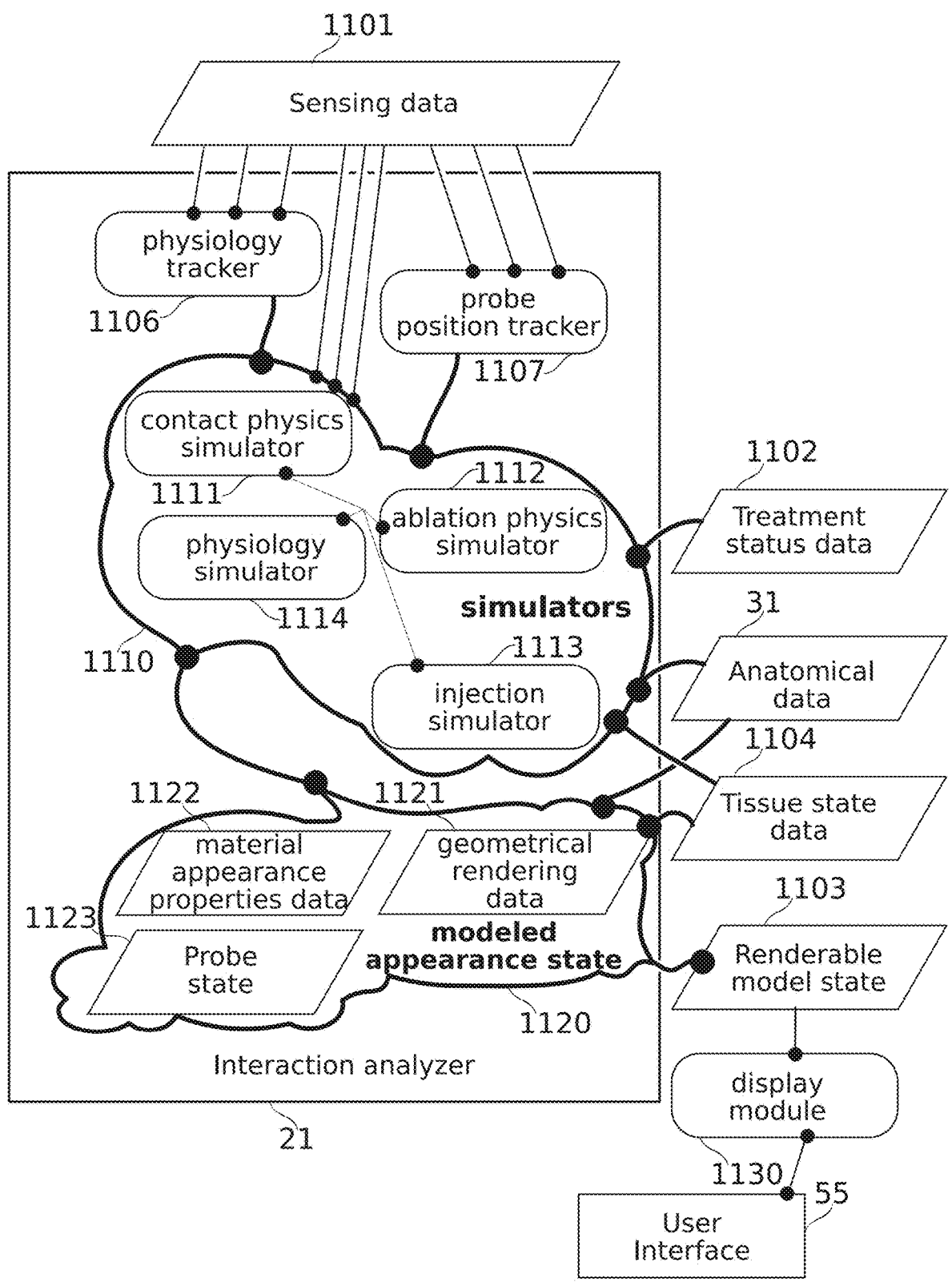
FIG. 7 schematically represents software components and data structures of an interaction analyzer of a system, according to some embodiments of the present disclosure.

In some embodiments, updating of the simulation scene during a procedure is at least partially based on data inputs from one or more data sources supplying data during the procedure (for example, sources of probe-tissue interaction data such as sensing data and/or treatment status data described in relation to FIG. 6 and FIG. 7). Graphical game engines typically receive inputs from game input devices such as pointer devices, keyboards, game controllers, body motion sensors, and the like. In some embodiments of the present invention, inputs optionally are from one or more additional or alternative inputs related to the performance of a catheter procedure—for example, catheter probe position data, data tracking the intrabody use of catheter probes (particularly but not exclusively use to deliver treatment; e.g. by delivering treatment energies), and/or measurement data, for example measurement data obtained from an intrabody probe (herein a catheter probe is used as an example of an intrabody probe, but it should be understood that another intrabody probe is optionally used in some embodiments; e.g., a capsule probe).

In typical applications of game engines, the simulated world (also referred to herein as a simulated scene) maintained by a game engine does not directly correspond to any simultaneous objective-world state. However, an object of some embodiments of the current invention is to simulate the reality of a clinical situation sufficiently to allow substantially seamless interaction with that reality via a presentation of the scene simulation. In some embodiments, this comprises maintaining and displaying a simulated scene having a useful level of correlation with the changing reality of the actual tissue environment (as reflected in data available to characterize it).

Optionally, usefulness derives from actions which are taken by an operator on the basis of information in the scene simulation presentation which reveals to a catheter operator the changing state of the tissue environment. Potentially, the useful level of correlation with the changing reality of the actual tissue environment allows an operator to realize the state of the tissue or a change in that state, optionally without adding to the scene annotations indicative of such state or state change. Optionally, usefulness derives from the presented scene simulation providing fidelity of representation sufficient that actions the operator takes based on the presented scene simulation produce effects as intended in the corresponding real-world environment. Optionally, the useful level of correlation with the changing reality of the actual tissue environment is a level of correlation sufficient to allow the operator to perform actions within the real-world environment based on the presented scene simulation. The presented scene simulation may include effects simulating results of the actions taken by the operator.

In some embodiments of the invention, a display of a user interface is updated at motion frame rate with rendered images of a simulation scene simulating an intrabody probe (for example, a probe at the end of a catheter) and its tissue environment. The updating optionally indicates changes to an actual intrabody probe and tissue environment which occur as an operator manipulates the actual intrabody probe (wherein the updating is based, e.g., on position data describing the position of the intrabody probe), and/or operates the intrabody probe for treatment and/or diagnostic measurement of the actual tissue environment (wherein the updating is based, e.g., on operational data describing operation of the intrabody probe to treat tissue and/or measure properties of the tissue). In some embodiments, changes are shown in the rendered images as if occurring within the actual material of the tissue environment.

For example, immediate and/or developing effects of ablation are shown by simulating appearance and/or geometrical changes in ablated tissue (in contrast, for example, to marks, icons, and/or symbols indicating ablation events). In some embodiments, tissue is deflected and/or an intrabody probe shape is distorted in rendered images of a simulation scene based on interaction data indicating touching contacts. These and other simulation scene changes (for example, other simulation scene changes as described herein) potentially provide an operator with a sense of presence in the actual tissue region accessed by an intrabody probe, and/or intuitive indications of changing status during a procedure underway.

In some embodiments, a smoothly updating, naturalistic appearance of a rendered view of a simulation scene is achieved even when available inputs indicating changes to the simulation scene are incomplete, slowly updating, irregular, and/or lagging (for example, as described in relation to FIG. 1B). Herein, "naturalistic" scene appearance means that the displayed scene gives an operator the impression of substantial materials (i.e., volume-occupying, as opposed to merely shell defining materials) and/or reactive materials existing in a fluidly navigable environment. The reactions of the materials in turn become a significant part of the information which an operator relies on to act within the actual environment that the scene simulates. A material moreover may be simulated as occupying volume per se (for example, as a wall having thickness), rather than merely as a boundary extending in space (for example, as a structure defining a surface, but having no well-defined thickness).

Optionally, appearances in rendered views of simulation scene objects are moreover "realistic" in some aspects. For example, tissues, in some embodiments, are provided with material appearances that mimic their appearance in life, and to this extent are "realistic". In some embodiments of the invention, for example, geometrical deformation of tissue in a simulation scene is directly based on deformation measurements, for example, ultrasound images of septal wall deflection during transseptal puncture are optionally converted into movements in three dimensions of a simulated septal wall's deflection.

However, non-realistic material appearances and even objects are optionally or additionally provided to a naturalistic scene. Degree of tissue compression, for example, is optionally used as a visual proxy for probe-tissue contact force (force of touching contact), whether or not the real tissue is indeed compressed.

In some embodiments of the invention, motion due to normal heart pulsations is indicated in the simulation by pulses with corresponding timing; this potentially helps an operator understand the difference between a probe in intermittent wall-touching contact and continuous wall-touching contact. Optionally, however, the amplitude of the simulated pulses is reduced from the real state, to stabilize the visual environment an operator uses for navigation. Additionally or alternatively, some geometrical states (such as degree of vasodilation and/or vasoconstriction) are optionally exaggerated for clarity.

In some embodiments, the size of one or more heart chambers is adjusted based on current heart rate, and/or the size and/or movements of a probe relative to the heart chamber are scaled based on current heart rate. It has been observed that as heart rate increases, the maximum size of the heart between contractions correspondingly decreases. This decrease can also be observed in the sizes adopted by heart chamber at other phases of the heartbeat cycle. For example, in some embodiments, the average rendered size of the heart over the course of a heartbeat cycle is decreased as a function of measured heart rate increase. The average size change is optionally to either a beating or non-beating rendered representation of the heart. Optionally heart wall thickness correspondingly increases with decreasing chamber size. It is a potential advantage to incorporate these dynamic changes in anatomy into a display used by an operator to guide an intrabody probe, and/or to improve the accuracy and/or precision with which actions by and/or through the probe (e.g., contacts and/or treatment administration) are associated to positions on the heart wall.

In another example, visual rendering of blood is preferably suppressed, making visualization possible from within a vascular or cardiac lumen. Optionally, one or more normally invisible tissue properties such as temperature are encoded by visual conventions; appearing as, for example in the case of temperature: ice, flame, smoke, and/or steam. In some embodiments, guiding marks related to planning and/or procedure progress are optionally provided as part of the simulation scene's naturalistic rendering to images.

Among the services provided by some prominent graphical game engines are motion physics simulators (e.g., for modeling collisions, accelerations, elastic deformations, object destruction, and the like). In some embodiments, one or more these motion physics simulators is used to increase the naturalistic impression and/or realistic fidelity of a rendered simulation scene. In some embodiments, one or more of these motion physics simulators is used to increase the naturalistic impression of a scene. Additionally or alternatively, geometrical deformations are used to indicate aspects of a procedure where a probe contacts tissue. As for the case of material appearances, the geometrical deformations may be, but are not necessarily realistic.

A general potential benefit of naturalistic (optionally also realistic) presentation of a scene comprising simulated tissue is to reduce cognitive load on a catheter operator and/or team of operators working with an intra-body probe. Such procedures typically have multiple interacting factors and requirements affecting procedure outcome. These factors and requirements preferably are tracked simultaneously and/or may need to be accounted for with little time for consideration. Examples of these factors and requirements in a standard operating environment optionally include any one or more of the following:

Positions of one or more probes are selected and verified with respect to a procedure plan.

Results of procedure actions are verified.

If planned actions and actual procedure actions begin to diverge, adjustments may be made on the fly.

Similarly, actual procedure results may not match planned results.

Some parts of the procedure optionally rely on discovering tissue states and locations, for example, based on sensing from the catheter probe.

Such discovery steps are preferably performed quickly and without undue repetition of catheter motions.

Particularly after plan and procedure diverge, relative timing of past procedure steps can be critical for deciding what current and/or following steps are optimal. For example, edema that gradually develops following lesioning (as in certain ablation procedures) can interfere with further lesioning, potentially leading to a need to adjust parameters and/or positions away from those first planned if there is a delay or error in an earlier phase of the procedure.

Similarly, the interpretation of sensing data is optionally dependent on the timing and/or results of previous actions. For example, a detected current impulse block in heart tissue may be correlated with the recent history of lesioning in an area to determine if the impulse block is more likely to be permanent (e.g., pre-existing, or in a well-lesioned area) or temporary (e.g., in a region where inactivation, for example, due to use of a lesioning modality, is potentially reversible).

In some embodiments of the current invention, immediate visual presentation of material appearance helps to control the complexity these factors can create. Potentially, a naturalistic display of information is more immediately understood by the clinical personnel, and/or intuitively draws attention to clinically relevant state updates. For example, instead of the operator team having to consider and/or calculate whether a previously lesioned tissue region was lesioned long enough ago to have converted to edematous tissue: in some embodiments, the edema is directly displayed as edematous tissue. Where a continuous lesion is planned, likely gaps in lesion extent can be directly seen in their overall context in the scene simulation, helping to guide the decision as to whether and/or how the procedure should be adapted to compensate.

A naturalistic presentation of catheter procedure information also contrasts, for example, with the presentation of this information using graphs and/or symbols. Familiarization with more abstract symbols, measures and graphs potentially requires prolonged training. An extra level of symbolic abstraction also potentially slows recognition by the physician of important changes in the state of the catheter interface or the tissue.

In some embodiments of the invention, a substantially continuous stream of input data describing a tissue region and/or probe interactions with it is used as a basis for correspondingly continuous updating of a scene simulating the tissue region. Optionally, the input data comprise only partial and/or indirect description of the tissue region. For example, spatially partial input data (such as from a cross-sectional image) is used in some embodiments to infer spatial changes over a larger region (such as a three-dimensional space extending outside the cross-sectional image). In another example, sensed pressure data from a catheter probe is optionally converted into corresponding movements in three-dimensional space of pressed-against tissue in the simulation scene. In some embodiments, effects on tissue by energy delivered from a lesioning probe are optionally simulated in a scene based on a model of energy dispersion in the tissue (e.g., thermal modeling, optionally thermal modeling incorporating information from anatomical data), and knowing a few parameters about how the energy was delivered (e.g., how long, with what energy, where, and/or with what efficacy).

In some embodiments, sensed input data is used as a basis for updating the state of the scene-representation of the probe itself. For example, sensed input data is used to adjust the position of the probe's scene representation, and/or to control the parameters of a viewpoint used in creating a rendered image of the simulation scene, wherein the viewpoint is defined by a position of the probe. In some embodiments, sensed input data (e.g., indicating tissue contact force and/or quality) is used as a basis for changing the shape of a simulated probe. The shape may be adjusted based, for example, on a mechanical model of the actual probe and/or a catheter or other device that carries the probe (e.g., a mechanical model which models the flexibility and geometry of the actual probe and/or associated carrying device). For example, some probes such as lasso electrode probes comprise a flexible portion that can be bent in response to the forces of touching contact. In another example, an otherwise stiff probe may be carried on a flexible member such as a catheter used to manipulate the probe. In some embodiments, sensed input data indicates forces applied to the actual probe, and the simulated probe is modified in response to the indicated forces according to the parameters of the mechanical model. The modification may also take into account other data, for example, a position of the probe itself, geometry of the chamber in which the probe is positioned, and/or a position of an aperture via which a probe is passed into a heart chamber or other body lumen. Potentially, the modeling allows a changing simulated probe shape to indicate changes to the actual intrabody probe in use, without requiring direct measurement of the actual intrabody probe's shape (e.g., by imaging).

Additionally or alternatively, in some embodiments, correlation between a simulation scene and the actual tissue region it represents is maintained at least in part by treating occasional inputs as describing events that (in the real world) trigger and/or entail certain predictable consequences to follow. In the simulation scene, the input optionally acts as a trigger for software routines that simulate those consequences. In some embodiments, longer-term effects of lesioning are optionally simulated by a physiological simulation. For example, a simulation converts estimated lesion damage into parameters for a script describing the gradual onset of tissue edema as it appears in rendered views of the simulation scene.

In some embodiments, moreover, partial and/or occasional inputs optionally guide calibration of the simulation scene maintained by the game engine so that it better-corresponds to the state of the actual tissue region. For example, sensing of tissue state or position directly using the probe as a sensing modality (additionally or optionally by another sensing modality, such as ECG, monitoring of patient hydration, or an intermittently acquired image) is optionally used to update a model state, potentially restoring and/or improving a degree of synchronization between the actual tissue region and the simulation scene.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Methods and Systems for Visual Modeling of Probe-Tissue Interactions and their Effects Reference is now made to FIG. 1A, which is a schematic flowchart illustrating the calculation and display of an image of a simulation scene, the simulation scene comprising simulated tissue having a geometry and/or geometrical appearance dynamically linked to interactions of the tissue with a catheter probe 11 (shown, for example, in FIGS. 3A, and 6), according to some embodiments of the present disclosure. In overview, a cycle of activities of the method includes, in some embodiments:

Receiving interaction data between probe 11 and tissue (at block 110).

Calculating geometrical effects altering a scene, the geometrical effects being indicated by the interaction data (at block 112).

Rendering the altered scene for visual presentation (block 114).

Illustrating examples of systems configured for carrying out this method, further reference is made to FIG. 6, which is a schematic representation of a system 1 configured to present interactions between a catheter probe 11 and a body tissue region 7, and/or effects of these interactions. System 1 is optionally configured to present the interactions and/or their effects at user interface 55. Reference is also made to FIG. 7, which schematically represents software components and data structures of an interaction analyzer 21 of system 1, according to some embodiments of the present disclosure.

Receipt of Interaction Data

The flowchart of FIG. 1A begins; and at block 110, in some embodiments, a system 1 (for example, the system 1 of FIG. 6) configured for display of interactions between a catheter probe 11 and a body tissue region 7 and/or results of such interactions receives interaction data. The interaction data may include, for example, data acquired by a sensing modality, and/or operation data of a treatment modality.

The interaction data, in some embodiments, comprise data indicating and/or numerically describing characteristics of interactions between probe 11 and tissue region 7; including, for example, positions of the probe and/or of contacts between the probe and the tissue region, contact characteristics characterizing a contact between the probe and the tissue region, measurements taken by the probe (for example, measurements of the physiological state and/or dielectric properties of the tissue region), and/or actions of the probe (e.g., operations comprising delivery of treatment). Optionally, interaction data comprise imaging data obtained during probe-tissue interactions.

System 1 of FIG. 6 indicates examples of sources of interaction data that are optionally provided in some embodiments of the present disclosure. Interaction data is optionally received in raw form, or in any suitable stage of intermediate processing to indicate a parameter and/or status of more direct applicability. With respect to FIG. 6, details for certain types of interaction data available in some embodiments of the invention (e.g., one type, all types, or any other combination of types) are now described for: position data, imaging data, dielectric tissue property sensing, general sensing (for example, of temperature and/or contact force), and treatment interactions.

Position Data:

In some embodiments (optionally), position data is sensed by use of an electromagnetic field navigation subsystem, comprising body surface electrodes 5, field generator/measurer 10, position analyzer 20, and sensing electrodes 3 (for example, sensing electrodes 3 located on catheter probe 11). The electromagnetic field navigation subsystem operates by inducing at least one time-varying electromagnetic (EM) field 4 (for example, three crossing EM fields, each of a different frequency) across a region of body 2 including a body tissue region 7 that is targeted to be navigated by catheter 9 and catheter probe 11. Typically, the time varying EM field is induced with a total inter-electrode voltage of one volt or less, at a frequency of between about 10 kHz and about 1 MHz. Voltages sensed at different positions by sensing electrodes 3 are characteristic of corresponding intrabody positions, allowing conversion by position analyzer 20, for example of voltage measurements to position information (for example, after exploration of an intrabody region 7 using the probe 11, and/or initially based on EM fields simulated with respect to a particular configuration of electrodes and anatomical data 31).

In some embodiments of the invention, position sensing at least partially comprises sensing of the relative position of a catheter probe 11 and a surface of tissue region 7; for example, by sensing of the dielectric environment of a sensing electrode 3 of catheter probe 11.

Imaging Data:

Additionally or alternatively, in some embodiments, there is provided an imaging modality 6, which may include, for example, an ultrasound modality and/or a fluoroscopy modality. Imaging modality 6 is configured to monitor body tissue region 7 during use of the catheter probe. Characteristics monitored by imaging modality 6 optionally comprise position information of the probe and/or of tissue affected by operation of the probe. In some embodiments, the imaging modality is in continuous, real-time (e.g., 5, 10, 15, 20, 30, 60 or more images per second) use during at least some phase of a procedure. Optionally, system 1 continuously processes changes in images produced by imaging modality 6 for immediate display (within a few milliseconds, for example, within 250 milliseconds) at user interface 55.

Additionally or alternatively, in some embodiments, imaging modality 6 operates less frequently (for example, once every minute to every five minutes, or at another interval). An infrequently updating imaging modality 6 is optionally used for providing periodic "key frames" used to synchronize and/or verify display of simulated states of tissue region 7 and/or catheter 9. Optionally, imaging information provides indirect information about elements in the scene simulation—for example, displacement of an organ boundary imaged with relatively high contrast optionally provides information about the displacement of a less clearly visualized organ in communication with the organ boundary. Also for example, data imaged in a tissue cross-section optionally provides information which can be extrapolated to regions outside of the cross-section. Optionally, an imaging modality is used only briefly during a procedure, for example, during a particular phase of a procedure such as a septal crossing.

Dielectric Tissue Property Sensing:

In some embodiments, dielectric property measurements (e.g., of impedance behavior of the electrical fields) providing indications of tissue state, and/or of tissue-probe contacts, are made by dielectric property analyzer 22. The measurements, in some embodiments, use sensing electrodes 3 (or a subset thereof) to determine impedance behavior of electromagnetic fields generated in conjunction with field generator/measurer 10, and optionally body surface electrodes 5. Dielectric distance sensing has already been mentioned in connection with the discussion of position data. Additionally or alternatively, in some embodiments, dielectric property sensing is used to distinguish, for example, the state of tissue as healthy, fibrotic, edematous, charred or charring, and/or electrophysiologically active (or capable of being so, e.g., retaining cellular integrity after attempted ablation). In some embodiments, dielectric property sensing identifies and/or verifies tissue type(s) in a sensed region. Dielectric property sensing for such properties is described, for example, in International Patent Application Nos. PCT/IB2016/052690 and PCT/IB2016/052686, the contents of which are incorporated by reference herein in their entirety.

General Sensing:

In some embodiments, other sensor information (sensed by optional other sensor(s) 14 on catheter probe 11) is used as interaction data. For example, a force sensor may provide information on contact between a catheter probe 11 and its environment. The information may include indication that the contact has happened, and optionally with what degree of force.

Additionally or alternatively, contact quality and/or contact force information is provided from sensing electrodes 3, based on impedance measurements and/or sensing of dielectric properties. For example, where a surface of tissue region 7 and an electrode 3 of a catheter probe 11 are in contact, dielectric sensing optionally is used to provide an indication of contact quality (optionally as related to a corresponding contact force), for example as described in International Patent Application No. PCT/IB2016/052686, the contents of which are included by reference herein in their entirety. Contact quality may include dielectric and/or impedance sensing of the tissue environment of one or more electrodes, based on which force, pressure, area, and/or angle of contact between electrodes and the tissue environment is inferred, relatively and/or absolutely.

In some embodiments, other sensor(s) 14 comprise a temperature sensor, flow sensor, and/or another sensor configured to provide information about the environment of the catheter probe 11.

Treatment Interactions:

In some embodiments, a treatment element 8 is provided on catheter probe 11. The interaction data (for example, treatment status data 1102 of FIG. 7) optionally comprises information about the operation of the treatment element and/or components controlling its effect (for example, power levels, activation events, timing settings, and/or substance amounts administered).

Treatment element 8 is optionally a probe for ablation treatment using an ablation modality; for example, one or more of the following ablation modalities: radio frequency ablation, cryoablation, microwave ablation, laser ablation, irreversible electroporation, substance injection ablation, and/or high-intensity focused ultrasound ablation. In some embodiments, treatment element 8 is also used as a sensing electrode 3 (for example, in RF ablation, a treatment delivery electrode may also be used to sense the effect of local dielectric properties on measured electrical field impedance). Optionally, treatment element 8 is operated in conjunction with a treatment controller 13, configured to provide treatment element 8 with functions such as power, control (e.g., of signal frequency, phase, and/or timing), and/or monitoring. In some embodiments, the treatment element 8 is configured to deliver a treatment other than ablation (for example, temporary activation or inactivation of tissue activity) using heat, cold, electrical current, sound radiation and/or light radiation.

Optionally, treatment element 8 comprises an injection apparatus, used to inject a treatment substance, and/or a substance used in diagnosis such an imaging tracer. In some embodiments, the injected substance comprises ethyl alcohol, Botox, living cells, and/or growth factor. Optionally, the injected substance comprises a radiolabeled substance, an immunosubstance, and/or a radiopaque trace substance. Optionally, treatment element 8 comprises a tool for manipulating tissue (e.g., grasping, holding, sampling, cutting, attaching, and/or suturing). Data indicating operations of treatment element 8 (and/or the rest of a treatment delivery system, for example, including a treatment controller 13) are optionally available within system 1, and in particular available to modules of interaction analyzer 21, as treatment status data 1102 (FIG. 7). It should be understood that treatment status data 1102 are not limited strictly to data about operations targeted to disease treatments as such, but optionally also include administration of substances and/or energy affecting a tissue region for a diagnostic purpose.

Interaction data relating to the interactions of a treatment element 8 with a target tissue region 7 include, for example, duration of operation, time of operation, nature and/or concentration of substances delivered, quantities of substances delivered, and/or power and/or frequencies of an exchange of energy between the treatment element 8 and tissue region 7 by a mechanism other than contact pressure (e.g., energy delivered for heating, energy removed for cooling, and/or energy delivered for disruption of structure). Optionally, operational settings are combined with information about the position and/or environment of treatment element 8 in order to derive interaction data. In some embodiments, such combination is performed by one or more of simulators 1110 of FIG. 7.

It should be understood that not every source of interaction data described in relation to FIG. 6 is necessarily implemented in every embodiment of the invention. Preferably, there is provided in embodiments of the invention at least a position sensing modality (e.g., comprising position analyzer 20), and a treatment modality which is monitored through treatment status data (e.g., comprising treatment controller 13). In FIG. 7, data from sensing indicated as sensing data 1101 optionally includes data from one or a plurality of sensing modalities; for example, sensor electrodes 3, other sensors 14, and/or imaging modality 6, described in relation to FIG. 6.

Moreover, it should be understood that computation-performing and/or control operation-performing modules are optionally implemented by any suitable combination of shared and/or dedicated processing units and/or controllers. For example, implementations of treatment controller 13, position analyzer 20, and/or interaction analyzer 21 optionally comprise one shared processing unit, or any other suitable number of shared and/or dedicated processing units.

Optionally, the flowchart continues with block 112. In some embodiments, certain types of interaction data (such as inputs indicating onset of ablation treatment) branch additionally or alternatively to FIG. 1B (dotted line branch indicates optional branching).

Geometrical Effects and Rendering of Virtual Materials

At block 112 of FIG. 1A, in some embodiments, geometrical effects which modify the apparent position of geometrical features in a rendered view of a simulation scene are optionally calculated for locations defined by a 3-D data structure representing geometry of the targeted body tissue region 7. The operations of block 112 are carried out, in some embodiments, by interaction analyzer 21 (detailed for some embodiments in FIG. 7). Optionally the geometrical effects of block 112 are calculated based on discrete events in the interaction data; for example, a single event such as a high-pressure contact triggering a tissue response like edema. Optionally, the geometrical effects of block 112 are calculated based on a history of interaction data; for example, a history of the delivery of ablation energy to a tissue region is used to estimate properties (for example, lesion extent) of an ablation lesion produced. The lesion properties are optionally estimated using a model of a thermal profile of the target tissue region and an estimate of temperatures/times at temperatures above which ablation occurs.

Figure 9A:
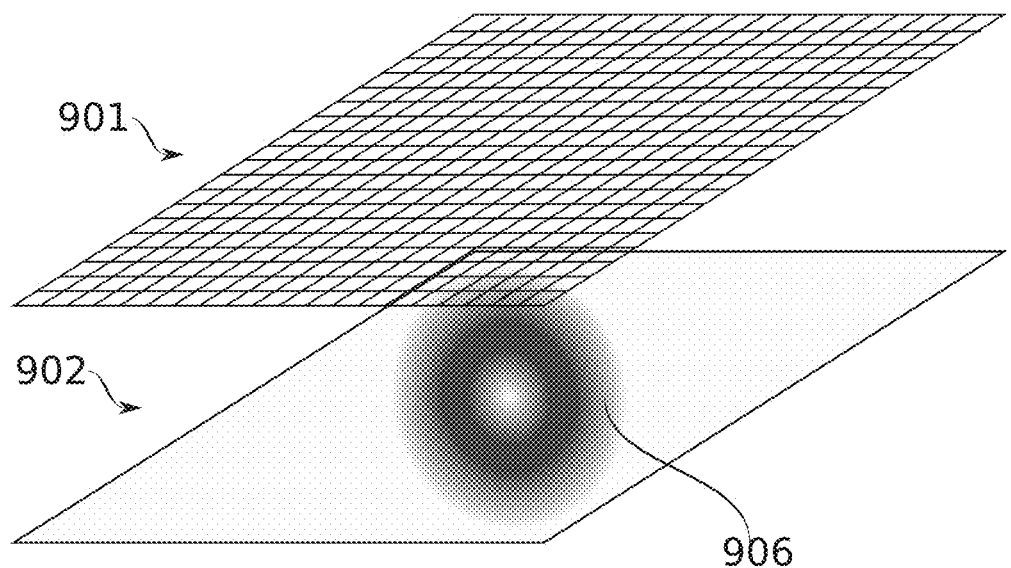
FIGS. 9A-9B schematically represent, respectively, different geometrical data representations of flat and indented surfaces, according to some embodiments of the present disclosure.
Figure 9B:
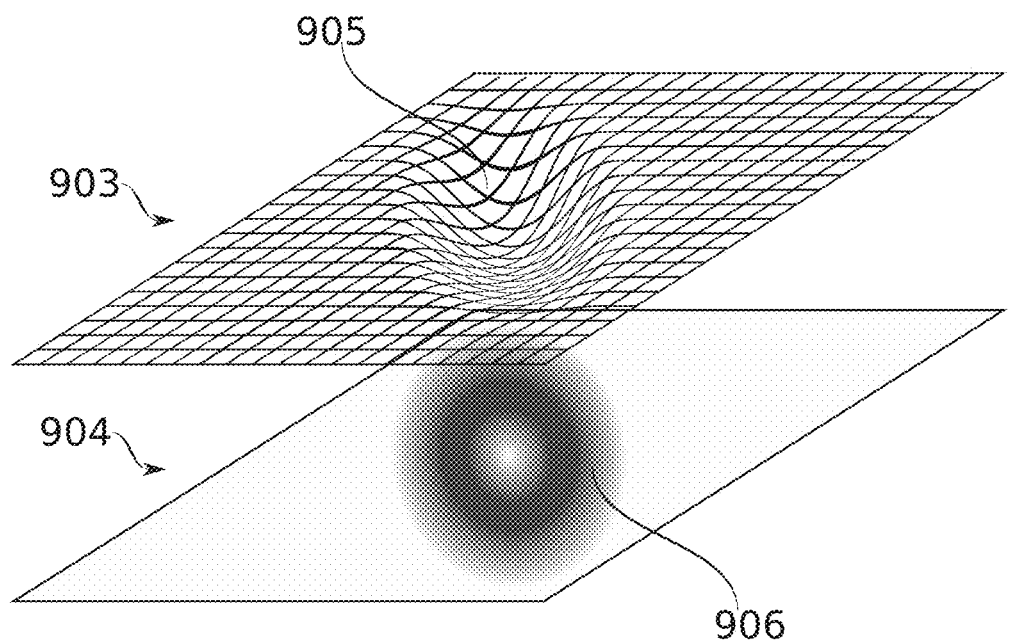

In further explanation of the distinction between adjustment of geometric points as such, and geometrical effects which affect the apparent position of geometrical points in a rendering, reference is now made to FIGS. 9A-9B, which schematically represent, respectively, different geometrical data representations of flat and indented surfaces, according to some embodiments of the present disclosure. The grids shown in the two figures to indicate geometrical point positions are illustrative; alternatively or additionally, these could be, for example: any set of geometrical points defined in a 3-D space by mesh data; by polygon definitions; and/or by one or more parametrically defined shapes such as polyhedra, ellipsoids, cylinders, planar-shape extrusions, and/or parametric curves. 3-D flat geometry 901 and indented geometry 903 (indented at indentation 905) represent the use of 3-D positions of geometrical points to visually convey surface shapes. The indentation 905, for example, is represented by displacing geometrically defined points falling within it by an appropriate distance out of the plane defined by other points of 3-D indented geometry 903.

Additionally or alternatively, geometrical appearance is changed (e.g., from a flat appearance to an indented appearance) by assigning to the surface of each rendered region within indentation 905 a suitable orientation (for purposes of rendering), chosen to optically mimic the angle the surface would have if the 3-D flat geometry 901 comprised a geometrically indented region like that of 3-D indented geometry 903; but without necessarily changing the 3-D geometry to which it maps. By convention, the surface orientation is represented by the orientation of a vector normal to (sticking straight out of) the surface.

For example, normal maps 902, 904 indicate by shading a changing elevation angle of a normal to the surface throughout region 906 (white is 90° elevation of the normal, while successively darker values represent successively decreased elevation values). Though not shown in the figure, normal maps 902, 904 preferably include representation of azimuth, e.g., azimuth mapped from 0°-360° around concentric circumferences of indentation 905. Surface orientation as represented by a normal map does not necessarily follow the geometrical surface orientation (for example, FIG. 9A shows a flat geometry 901 paired to a normal map 902 that represents an indentation). Though the resulting appearance change is not shown in FIGS. 9A-9B, FIGS. 10A-1B do provide an example of how a geometrical appearance can be changed (in that case to appear like a raised bump) by use of shading, without necessarily changing underlying geometrical positions.

To render the effects of a normal map, a rendering pipeline typically takes into account at least the relative angle of each surface normal and a light source in order to determine how much light is received at the camera. Then, for example (and other things being equal): when the relative angle is low, the surface is brighter; when the relative angle is high, the surface is darker. Optionally, the normal mapping algorithm also takes into account camera position and/or viewing angle-dependent surface reflection/scattering properties of the surface.

Normal mapping uses include, for example: to create the appearance of surface irregularities where the 3-D geometrical data has none, to exaggerate the 3-D appearance of shapes in the 3-D geometrical data, and/or to smooth transitions between polygons where the 3-D geometrical data describes abrupt changes (for example, between polygons in a mesh). In connection with some embodiments of the present invention, normal mapping (and a normal map, supplied as part of the geometrical rendering data 1121) has particular application for the showing of tissue deformations such as swelling (e.g., to indicate tissue damage) and indentation (e.g., to indicate probe-tissue contact). Embodiments optionally implemented with the use of normal mapping are described, for example, in relation to FIGS. 10A-10B, 10C-10D, 4A-4D, and 5A-5B. A distinction is drawn between the use of normal mapping techniques to define and/or highlight surface features having functional significance to an ongoing catheterization procedure, and the use of normal mapping techniques to provide general texture (such as bump mapping), and/or to mask display artifacts (such as masking of geometrical mesh artifacts using Gouraud shading or Phong shading).

Herein, 3-D structure rendered in a scene (in particular, 3-D data defining organ structure) is geometrically represented by geometrical rendering data 1121. 3-D positions are one part of the geometrical rendering data. Data used to affect geometrical appearance such as by use of normal maps (apart from use to define fine-grain texture) are considered to comprise a second part of the geometrical rendering data 1121.

In some embodiments, the geometrical rendering data 1121 comprise mesh data; for example as commonly used in defining structures for computerized visual rendering of 3-D structures. Geometrical rendering data 1121 specify positions (and usually also connections among positions, and/or positions joined by the extent of a common surface and/or material volume), corresponding to positions of surfaces of a target body tissue region to be visually rendered for presentation. Optionally, the geometry of positions interior to the surface is also defined and/or represented. For example, presentation optionally includes the use of transparency and/or cross-sectional views, whereby an interior portion of a tissue region is made visible.

Surfaces represented are optionally external (e.g., organ surfaces; not necessarily surfaces visible externally to the body) and/or internal (e.g., lumenal) surfaces of the target body tissue region. In some embodiments, geometrical rendering data 1121 are derived from anatomical data 31; for example, appropriately segmented 3-D medical image data. In some embodiments, anatomical data 31 include specification of tissue region thicknesses, for example, thicknesses of heart walls. Heart wall thickness is optionally obtained from, for example: atlas information (optionally for a population corresponding to the current patient), modified atlas information (for example, scaled according to anatomical landmark correspondence, heart rate, and/or point observations), and/or imaging of the patient (for example, one or more of CT, MRI, and/or nuclear imaging techniques).

Moreover, in some embodiments, the appearance of the raw geometrical rendering data 1121 that is finally presented by a user interface 55 is also determined in part by the assignment to the geometry of material appearance properties (MAPs); that is, properties affecting the appearance of materials represented in the rendered image. As the term is used herein, MAPs comprise any properties associated to positions (typically positions of a "virtual material", as next described) in a virtual environment for visual rendering according to simulated optical laws, and which affect how a surface and/or its enclosed volume are visualized within a 3-D rendered space. For example, MAPs may define color, texture, transparency, translucency, scattering, reflectance properties, and the like. MAPs are usually but not only assigned to surface positions defined by the geometrical rendering data. MAPs are optionally assigned to volumes defined by surfaces specified by the geometrical rendering data 1121. MAPs can also be assigned to the virtual environment (e.g., as lighting parameters) in such a way that they selectively affect material appearance at different positions. In some embodiments of the current invention, MAPs are used to in part define surface textures, for example by use of bump mapping (a type of normal mapping technique).

Creating the visual rendering in some embodiments may include surfaces and/or volumes comprising "virtual material"; for example, a virtual material having a visual appearance of myocardial tissue, and used in the representation of a heart wall defined by two surfaces. A virtual material, in some embodiments, is subject to simulated optical rules approximating processes such as reflection, scattering, transparency, shading, and lighting. Not every optical rule used in visual rendering is a copy of a real-world physical process; the art of computer rendering includes numerous techniques (for achieving both realistic and deliberately unrealistic results) that apply simulated optical rules that have no direct physical equivalent. Normal mapping has already been mentioned as a technique which can be applied to change a texture and/or geometrical appearance. Another example of a simulated optical rule is ambient occlusion. Ambient occlusion is an efficiently calculable method of simulating the effect of ambient lighting, but the occlusion is defined as a mapped property of an object's surface, rather than as an effect of light emitted from positions in the environment.

A virtual material optionally also defines material properties that are not directly either geometrical or "of appearance", for example, density, viscosity, thermal properties, and/or elastic properties. Insofar as these properties do in turn (in a given embodiment) affect the definition of MAPs (for example, via calculations of one or more simulators 1110), they are optionally treated as parts of material appearance properties data 1122, without actually comprising MAPs in themselves. Additionally or alternatively, non-appearance properties, particularly those that affect how geometry changes (such as thickness, density, velocity, viscosity, and/or elasticity), are optionally considered part of the geometrical rendering data 1121 insofar as they affect geometrically apparent behaviors of the material (e.g., how the material changes in shape).

Calculation of Geometrical Effects from Interaction Data

In some embodiments of the invention, geometrical effects of tissue-probe interactions on a simulated tissue region are assigned based on the output of one or more simulators 1110 (FIG. 7).

In some embodiments, sensing data 1101 and/or treatment status data 1102 (i.e., data describing the operation of a treatment modality) are used directly or indirectly as input to one or more simulators 1110 (e.g., simulators 1111, 1112, 1113, and/or 1114) that make adjustments to a modeled appearance state 1120 of the tissue based on inputs received, and one or more simulated aspects of tissue physiology, geometry, and/or mechanics. The modeled appearance state 1120 includes the geometrical rendering data 1121 and material appearance properties data 1122 in a form suitable for being operated on by the simulators 1110; it may also be or comprise a renderable model state 1103 suitable for rendering for presentation, or else be convertible to a renderable model state 1103. In some embodiments, modeled appearance state also includes data indicating the probe state 1123.

Simulators 1110 also optionally receive as starting input anatomical data 31 and/or tissue state data 1104. In addition to adjusting the modeled appearance state 1120, simulators 1110 optionally maintain their own internal or mutually shared simulation states. In some embodiments, simulators 1110 use motion simulation services exposed by a graphical game engine that can produce geometrical changes to a scene based, for example, on simulated collisions among scene elements, gravity effects, velocity, momentum, and/or elasticity.

Operations of some exemplary simulators 1111, 1112, 1113, and/or 1114 are described in the context of the examples of FIGS. 2A-2E, 3A-3L, 4A-4D, 5A-5B, 10A-10B, and 10C-10D.

In relation to FIG. 7, different input types providing probe-tissue interaction data as input to simulators 1110 are now described, including direct sensing input, physiologically interpreted sensing input, positionally interpreted sensing input, and treatment status input. In some embodiments, the inputs comprise direct and/or transformed use of one or more of the interaction data types described in relation to block 110.

Direct Sensing Input:

In some embodiments, adjustment of the simulation scene is implemented based directly on sensing data 1101. For example, a pressure reading from a pressure sensor 14 is optionally mapped directly to a geometrical displacement according to the measured pressure.

Additionally or alternatively, in some embodiments, a more involved simulation is performed; wherein probe interaction with a virtual material representing tissue is, in at least one aspect, physically and/or physiologically simulated in order to produce a new modeled appearance state.

Physiologically Interpreted Sensing Input:

In some embodiments, the use of sensing data 1101 by a simulator is indirect after interpretation by one or more physiology trackers 1106. Physiology tracker 1106, in some embodiments, is a module which accepts sensing data 1101 and generates an assessment of current physiological state based on the sensing data 1101. For example, in some embodiments, sensing data 1101 comprises dielectric measurements that physiology tracker 1106 is configured to convert into assessment of tissue state, for example fibrotic, healthy, or edematous; for example as described in International Patent Application No. PCT/IB2016/052690, the contents of which are included by reference herein in their entirety. Optionally or alternatively, electrical activity originating in tissue indicating a functional state (e.g., general capacity to support electrical activity, and/or feature of the activity itself) is measured and used as sensing input.

The output of the physiology tracker 1106 from one or more of these inputs is optionally in terms of one or more states such as tissue thickness (e.g., heart wall thickness), lesion depth, lesion volume, degree of lesion transmurality, characterization of tissue edema, characterization of functional activity and/or inactivation, a classification as to a potential for tissue charring, and/or a classification as to a potential for or occurrence of steam pop. "Steam pop" is a phenomenon occurring during ablation with an audible popping noise and/or spike in impedance, which is apparently due to sudden release of steam after excessive heating, associated with risk of perforation.

These outputs are optionally provided to a physiology simulator 1114 and/or an ablation physics simulator 1112, configured to convert such states into MAPs, other virtual material properties, and/or geometrical effects that indicate the tissue state(s) calculated from the measurements. Optionally, the tissue state interpreted from the sensing input also affects mechanical properties used, for example, by a contact physics simulator 1111 and/or an injection simulator 1113. It is a potential advantage to implement a physiological tracker 1106 as a distinct module that can be treated as a computational "service" to any appropriate simulator 1110. However, it should be understood that physiological tracker 1106 is optionally implemented as part of one or more simulators 1110 producing changes to a modeled appearance state 1120. In this case, the module configuration is more like that of direct sensing input, with the simulation of appearance integrated with physiological interpretation of the sensing data.

Positionally Interpreted Sensing Input:

In some embodiments, the use of sensing data 1101 by a simulator is indirect after interpretation by a probe position tracker 1107. Probe position tracker 1107, in some embodiments, is a module that accepts appropriate sensing data 1101 (e.g., electromagnetic field navigation data, acoustic tracking data, and/or imaging data) and converts it to a measurement of the position (e.g., a measurement of the location and/or a measurement of the orientation) of a probe such as catheter probe 11, for example as described in International Patent Application No. PCT/IB2016/052687. It optionally comprises position analyzer 20. Optionally, position tracker 1107 implements processing to massage outputs of position analyzer 20 in view of the current state of the scene simulation—for example, to recalibrate sensed position data to positions compatible with the scene simulation. Optionally, position tracker 1107 integrates position data from a plurality of position inputs.

Optionally position determination includes determination of tissue contact force and/or quality, using a force sensor on the probe, and/or for example as described in International Patent Application No. PCT/IB2016/052686, the contents of which are included by reference herein in their entirety. Additionally or alternatively, on-line imaging data (e.g., ultrasound and/or angiographic images) are used, intermittently and/or continuously, to determine and/or verify probe position.

Probe position determinations are optionally used as inputs to any of simulators 1110; for example in order to assign particular positions to measurements of other tissue states/properties, and/or to help characterize changes induced by probe interactions with tissue (e.g. geometrical distortions of tissue introduced by touching contact with the probe, and/or simulated effects of treatment procedures). It is a potential advantage to implement probe position tracker 1107 as a distinct module that can be treated as a computational "service" to any appropriate simulator 1110. However, it should be understood that probe position tracker 1107 is optionally implemented as part of one or more simulators 1110 producing changes to a modeled appearance state 1120 maintained by interaction analyzer 21.

Treatment Status Input:

In some embodiments, simulation is implemented based on treatment status data 1102. Treatment status data 1102 include data indicating the operation and/or status of a treatment modality—for example, power, control parameters (e.g., of signal frequency, phase, and/or timing), and/or monitoring data. Optionally, treatment status data are applied directly to modeled appearance state 1120; for example, as an indentation or other deformation at a position of treatment modality activation. Additionally or alternatively, in some embodiments, at least one aspect of the tissue and/or tissue/probe interaction is physically and/or physiologically simulated in order to produce a new modeled appearance state 1120, based on the treatment status data.

For example, in some embodiments, a physiology simulator 1114 receives input indicating that a probe-delivered treatment operation has occurred at some particular position (optionally along with parameters of the treatment operation). Physiology simulator 1114 is optionally configured to model the reaction of tissue to the treatment, instantaneously (for example, due directly to energy delivered by an ablation treatment), and/or over time (for example, as an edematous reaction develops in the minutes following an ablation treatment). In another example, an injection simulator 1113 receives treatment status data indicating that a material injection is occurring. Injection simulator 1113 is optionally configured to model an appropriate reaction of tissue to the injected substance (e.g., swelling to indicate the injected volume, and/or to indicate injury response to the injection). The reaction is optionally immediate, and/or includes a slow-developing component as the material diffuses from the injection site. Optionally, changes in geometry due to the addition of material volume to the tissue are also modeled.

Presentation of Visual Rendering

At block 114, in some embodiments, a rendering of the modeled appearance state is created for presentation.

In some embodiments of the invention, geometrical effects on a simulated tissue region are assigned based on the output of one or more simulators 1110 (FIG. 7).

In some embodiments, sensing data 1101 and/or treatment status data 1102 are used directly or indirectly as input to one or more simulators 1110 (e.g., simulators 1111, 1112, 1113, and/or 1114) that make adjustments to a modeled appearance state 1120 of the tissue based on inputs received, and one or more simulated aspects of tissue physiology, geometry, and/or mechanics. Simulators 1110 also optionally receive as starting input anatomical data 31 and/or tissue state data 1104. In addition to adjusting the modeled appearance state 1120, simulators 1110 optionally maintain their own internal or mutually shared simulation states. In some embodiments, simulators 1110 use motion simulation services exposed by a graphical game engine that can produce geometrical changes to a scene based, for example, on simulated collisions among scene elements, gravity effects, velocity, momentum, and/or elasticity.

Operations of some exemplary simulators 1111, 1112, 1113, and/or 1114 are described herein in the context of the examples of FIGS. 2A-2E, 3A-3L, 4A-4D, and 5A-5B.

In some embodiments of the invention, a modeled appearance state 1120 is converted to a renderable model state 1103 and provided to a display module 1130 that converts (renders) the renderable model state into at least one image comprising a visually rendered representation of the intrabody region 7. Optionally, modeled appearance state 1120 is directly represented as a renderable model state 1103 (this is a potential advantage for tighter integration of the simulation with a game engine driving its rendering and presentation). The at least one image is displayed by one or more graphical displays of a user interface 55. User interface 55, in some embodiments, comprises one or more displays, for example a computer monitor, virtual reality goggles, and/or 2-D or 3-D projection device. Preferably, user interface 55 also comprises one or more user input devices that can be used for tasks such as selecting operating modes, preferences, and/or display views. It is noted that insofar as catheter probe position sensing affects simulation and/or display, catheter probe manipulation also acts as a special form of user input device; but for purposes of the descriptions herein such catheter probe sensing inputs should be considered distinct from inputs provided through user interface 55.

In some embodiments, the display module 1130 renders from one, two, three, or more viewpoints simultaneously. In some embodiments, rendering is performed (and the resulting images are displayed) at a frame rate sufficient to produce perceived motion (herein, such a frame rate is termed a motion frame rate)—for example, at least 10-15 frames per second; and optionally at least, for example, 15, 20, 30, 50, 60, or 100 frames per second (fps), or another greater or intermediate value. Within this range, lower frame rates (e.g. 10-20 fps) tend to give the appearance of "choppy" motion, with apparent motion growing increasingly fluid with rates up to at least 30-60 fps. More fluid motion is potentially less fatiguing and/or more precise for guiding actions based on events in the simulation scene. Still higher frame rates (above the nominal frequency of visual flicker fusion) add the potential advantage of increasingly convincing presentation of very rapid motion (e.g., reducing visual appearance of discrete-position motion "trails"). Trans-flicker fusion frequency frame rates are optionally preferred for immersive, virtual reality (VR) user interface implementations; higher frame rates potentially help mitigate VR motion sickness.

In some embodiments of the invention, display module 1130 includes a computer-implemented software module comprising the rendering pipeline 1230 of a 3-D graphics engine 1200 (software environment) such as is provided with graphical game engines such as the Unreal® or Unity® graphical game engine, or another game engine. Some general aspects of 3-D graphical game engines are discussed in relation to FIG. 8, herein. Optionally, the conversion of a modeled appearance state 1120 into a renderable model state 1103 comprises the creation and/or instantiation of computer data and/or code structures that are directly used by the rendering pipeline of the 3-D graphics engine 1200.

Optionally, some functions of interaction analyzer 21 (for example, any of simulators 1110) are provided as functions (e.g. classes, hook implementations, etc.) making use of the application programming interface (API) of such a 3-D graphics engine 1200.

Ending the presentation of FIG. 1A: at block 116, in some embodiments, flow optionally returns to block 110 to receive more interaction data, or else (if adaptive visual rendering is to be suspended), the flowchart ends.

Use of a Graphical Game Engine in Real-Time Anatomical Navigation

Continuing reference to FIG. 7, in some embodiments of the invention, geometrical effects on a simulated tissue region are assigned based on the output of one or more simulators 1110.

In some embodiments, sensing data 1101 and/or treatment status data 1102 are used directly or indirectly as input to one or more simulators 1110 (e.g., simulators 1111, 1112, 1113, and/or 1114) that make adjustments to a modeled appearance state 1120 of the tissue based on inputs received, and one or more simulated aspects of tissue physiology, geometry, and/or mechanics. Simulators 1110 also optionally receive as starting input anatomical data 31 and/or tissue state data 1104. In addition to adjusting the modeled appearance state 1120, simulators 1110 optionally maintain their own internal or mutually shared simulation states. In some embodiments, simulators 1110 use motion simulation services exposed by a graphical game engine that can produce geometrical changes to a scene based, for example, on simulated collisions among scene elements, gravity effects, velocity, momentum, and/or elasticity.

Operations of some exemplary simulators 1111, 1112, 1113, and/or 1114 are described in the context of the examples of FIGS. 2A-2E.

Figure 8:
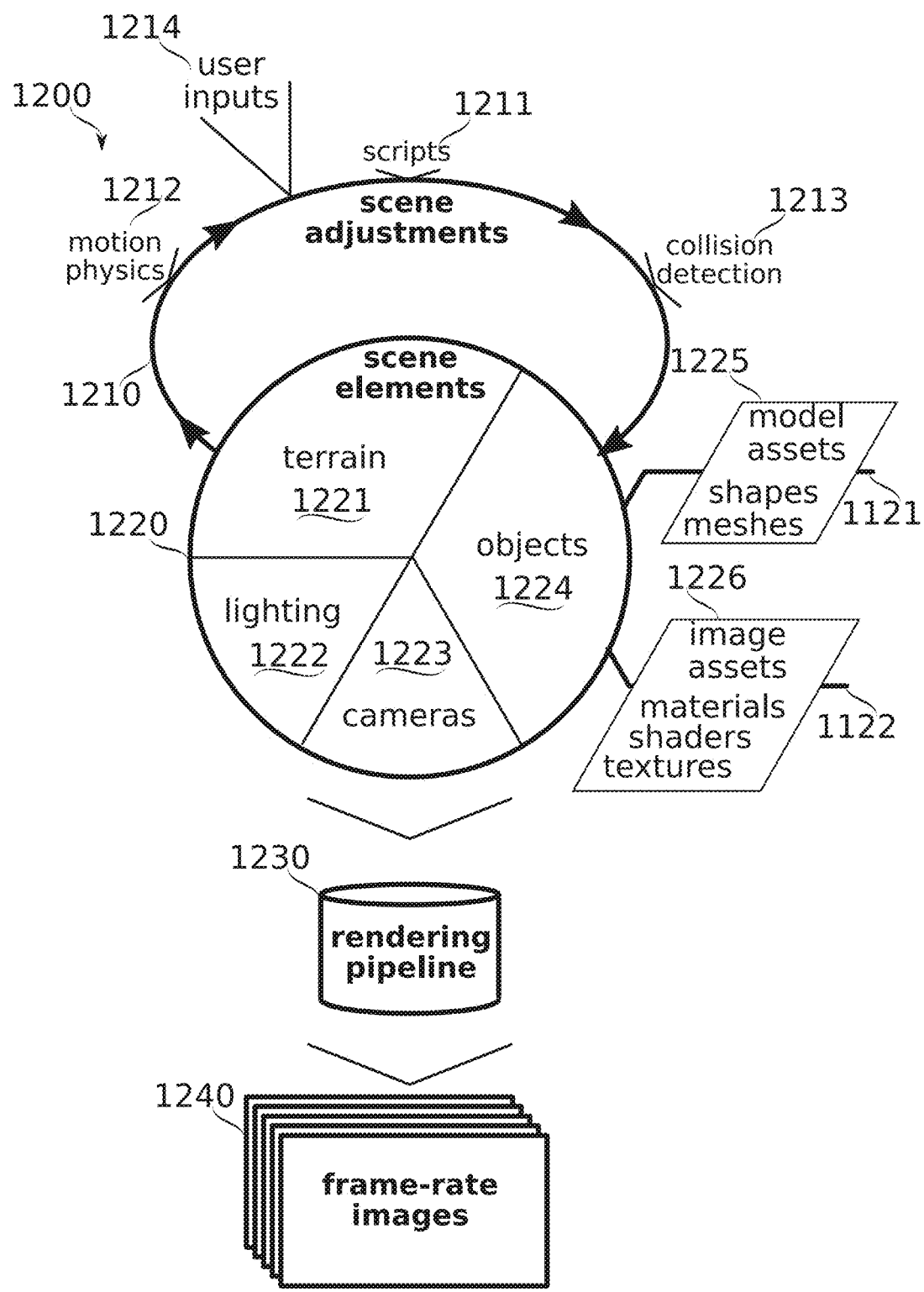
FIG. 8 schematically represents components, inputs, and outputs of a graphical game engine operating to manage and render scene elements to images for presentation at motion frame-rate, according to some embodiments of the present disclosure.

Reference is now made to FIG. 8, which schematically represents components, inputs, and outputs of a graphical game engine 1200 operating to manage and render scene elements 1220 to motion frame-rate images 1240, according to some embodiments of the present disclosure.

In some embodiments of the invention, a graphical game engine 1200 is used not only to render images (for example as described in relation to block 114 of FIG. 1A), but also to provide more generally the data structure and code framework of the "scene" and how it changes in response to time and/or input.

In broad outline, a graphical game engine 1200 comprises a collection of computer software components exposing one or more application programming interfaces (APIs) for use in describing, instantiating (initializing and maintaining), continuously updating, rendering, and/or displaying of scene elements 1220. Examples of graphical game engines include the Unreal® and Unity® graphical game engines.

The scene elements 1220 provided for the operations of graphical game engine 1200 optionally include, for example, descriptions of terrain 1221, objects 1224, cameras 1223, and/or elements for lighting 1222. In some embodiments of the present disclosure, definitions of scene elements 1220 are derived from geometrical rendering data 1121 and/or MAPs data 1122. Definitions are optionally expressed in terms of geometrical-type scene data 1225 (e.g. model assets, shapes, and/or meshes), and/or appearance-type scene data 1226 (e.g., image assets, materials, shaders, and/or textures). In some embodiments, geometrical rendering data 1121 and MAPs data 1122 are initially produced already in a format that is directly used by graphical game engine 1200.

In some embodiments, scene elements 1220 are provided with simulated dynamic behaviors by an iterated series of calculated scene adjustments 1210. Scene adjustments 1210 are optionally implemented by a variety of software components for e.g., motion physics services 1212, collision detection service 1213, and/or scripts 1211. These are examples; graphical game engines 1200 optionally implement additional services, e.g., "destructibility". Scripts 1211 can be provided to simulate, for example, autonomous behaviors and/or the effects of triggered events. Scripts 1211 are optionally written in a general-purpose computer language taking advantage of APIs of the graphical gaming engine 1200, and/or in a scripting language particular to an environment provided by the core graphical gaming engine 1200. Graphical gaming engines optionally also accept integration with plugin software modules (plugins, not shown) that allow extending the functionality of the core graphical game engine 1200 in any of its functional aspects. For purposes of the descriptions provided herein, plugins that perform functions related to updating the scene state are also encompassed within the term "script" 1211. In some embodiments, all or part of any of simulators 1110 is implemented as a script 1211.

For purposes of descriptions herein, scripts 1211 (optionally including plugins) and scene elements 1220 are considered part of the graphical game engine 1200 as a functional unit. Optionally, for example where reference is made particularly to the off-the-shelf graphical game engine apart from specialized adaptations for uses described herein, the term "core graphical game engine" is used.

For interactivity, graphical game engines 1200 accept user input 1214 (optionally including, but not limited to, inputs from user interface 55 devices such as mouse, keyboard, touch screen, game controller, and/or hand motion detector; and for some embodiments of the current invention, optionally including data provided as input that indicate probe positions, treatment modality operation, etc.).

A typical graphical game engine also includes a rendering pipeline 1230 that may include one or more stages of 3-D rendering, effects application, and/or post-processing, yielding at least one stream of frame-rate images 1240. In some embodiments, the stages of the rendering pipeline 1230 include modules that implement simulated optical algorithms—not necessarily directly based on real-world physical laws—generally selected to produce a rendered result that visually gives to elements in the rendered scene the appearance of material substances.

Table 1 includes some examples of how graphical game engine features and concepts are optionally used in some embodiments of the current invention:

TABLE 1

Examples of Graphical Engine Feature/Concept Usage

| FEATURE/CONCEPT | EXAMPLES OF USE |
| --- | --- |
| Scene | Overall visually renderable model of environment and objects within it. Optionally equivalent to a renderable model state 1103 and/or scene elements 1220. |
| Terrain | Optionally used to represent geometry of the anatomical environment; e.g., geometrical rendering data 1121. For example, the heart wall might be implemented as terrain 1221 (alternatively, anatomical features are implemented as objects 1224; e.g., as mesh geometry objects, and/or combinations of primitive objects such as cylinders, boxes, and/or ellipsoids). |
| Objects 1224 | Probe 11 is optionally represented as a "game" object, and may optionally serve as a viewpoint anchor like avatars and/or tools in certain 3-D games. Significant features of the anatomical environment such as scars, lesions, and/or regions of edema, are optionally implemented as appropriately positioned objects, e.g., embedded in an environment of surrounding tissue. Guides and markers are optionally implemented as game objects. |

TABLE 1-continued

Examples of Graphical Engine Feature/Concept Usage

| FEATURE/CONCEPT | EXAMPLES OF USE |
| --- | --- |
| Assets | Tissue, probe, guide, and/or other objects and/or their appearances are optionally instantiated from assets that represent available types of objects, their behaviors and/or their appearances. Optionally includes geometrical-type scene data 1225 (e.g. model assets, shapes, and/or meshes), and/or appearance-type scene data 1226, (e.g., image assets, material, shaders, and/or textures). |
| Cameras 1223 | Cameras optionally define flythrough viewpoint(s) of the anatomy traversed by the catheter probe 11, and/or overview viewpoint(s) (showing probe and tissue from a remote viewpoint). Optionally, the position of catheter probe 11 defines one or more camera viewpoints by its position/or orientation. |
| Lighting 1222 | In addition to providing general lighting of the tissue being navigated, lighting 1222 is optionally defined to provide highlighting, e.g., of regions pointed at by probe 11, indications of environmental state by choice of light color, light flashing, etc. Lighting is optionally used to implement MAPs non-locally (that is, a defined light source optionally is defined to illuminate a view of simulated tissue to selectively change its material appearance, while not being part of the material properties of appearance of the simulated tissue as such). |
| Image Assets; Materials, Shaders, and Textures 1226 | MAPs that are also material properties of appearance, for example, defining the appearance of tissue as healthy muscle, edematous, fibrotic, heated, cooled, etc. |
| Particle Systems | Type of object optionally used for providing effects such as smoke/steam-like indications of ablation heating, spray, transfer of energy, etc. |
| Collision Detection Service 1213 and Motion Physics Service 1212 | Optionally used for interactions between probe and the geometry of the anatomical environment; optionally including deformation of the probe and/or the anatomy. As implemented by core graphical game engines, the term "physics" generally is limited to physics affecting movement/deformation of game objects such as collision, gravity, or destruction. In some embodiments, simulators 1110 include simulation of other "physics", such as temperature, physiological change, etc. |
| Scripts 1211 | Optionally used for animating and/or showing changes in dynamic features of the environment (lighting, terrain), view (camera position) and/or game objects, optionally gradually over a period of time: for example, development of lesions, development of edema, heating/cooling effects, and/or injection effects. Optionally, scripts are used to implement dynamic appearance, even though the underlying state representation is constant (e.g., coruscating and/or pulsing effects). |
| User Input 1214 | Optionally comprise inputs reflecting changes in probe position (e.g., output of probe position tracker 1107) for guiding navigation through the scene, and/or determining camera position. Some treatment status data 1102 are optionally interpreted as inputs reflecting operator interaction with the scene. |
| Multiplayer | During a procedure, there are optionally a plurality of different operators working simultaneously with a system according to some embodiments of the current invention. For example, while a primary physician manipulates the intra-body probe, one or more additional workers are optionally reviewing the simulated environment to locate next target sites for the probe, evaluate effects of previous ablations, etc. Optionally, there is more than one probe in use at a time, each of which is optionally treated as a different "player" with its own associated camera views and/or interaction capabilities. |

Independently Time-Evolving Probe-Tissue Interactions

Reference is now made to FIG. 1B, which is a schematic flowchart illustrating the calculation and display of an rendered image of a simulation scene comprising a view of simulated tissue having a geometry and/or geometrical appearance of a tissue dynamically changing as a function of time to represent changes developing subsequent to a triggering interaction between the tissue and a catheter probe, according to some embodiments of the present disclosure.

In some embodiments of the invention, simulation of probe-tissue interactions includes simulation of tissue effects (e.g., injury response) developing substantially independently of continuing inputs from probe-tissue interaction data. In some embodiments, the flowchart of FIG. 1B branches off from certain input cases of the flowchart of FIG. 1A, wherein geometrical effects develop at least partially concurrently with (and optionally unsynchronized to) geometrical effects which immediately track changes in inputs.

In FIG. 1B, initial interaction data is received (optionally entering the flowchart from block 110 of FIG. 1A). After this, the simulated geometry evolves according to the results of pre-set rules which operate substantially independently of further input for a time. A potential advantage of this approach is to allow continuously updated visualization of tissue changes, even when no new sensing data has been obtained to confirm them.

The flowchart optionally begins after a triggering probe-tissue interaction has occurred which is to be modeled as provoking changes to the scene which continue after the trigger time $t_0$. For example, an input indicating that ablation energy has been delivered triggers the operations of the flowchart.

Optionally, operations of the flowchart of FIG. 1B are implemented by a script 1211. Additionally or alternatively, operations of the flowchart are implemented by a simulator 1110, for example, physiology simulator 1114.

At block 120, in some embodiments, one or more geometries and/or geometrical appearances are set to an initial state (an existing state is optionally used as the initial state) and a simulation function is selected and assigned to change the geometries and/or geometrical appearances as a function of time according to parameters set from inputs describing the probe-tissue interaction. These inputs may be included in the interaction data received at block 110. In some embodiments, the simulation function is configured to evolve according to the state of a timer.

For example, in some embodiments, a physiology simulator 1114 is configured to emulate effects of edema developing post-ablation, based on parameters such as the position, amount of energy delivery, and/or duration of energy delivery causing the ablation. Edema is optionally modeled to develop over the course of several minutes (for example, 2, 5, 10, 15, 20 or another number of minutes). Optionally, modeled changes in geometry and/or geometrical appearance simulate changes in muscle tone, e.g., vasodilation or vasoconstriction. The geometry and/or geometrical appearance is optionally modeled to show thickening and/or thinning, increase and/or decrease in surface height variation over a surface area, and/or another deformation, for example: dimpling, puckering, "goose-pimpling", stretching, collapsing, expanding, distending, and/or shrinking. Lumenal structures optionally show change in cross-sectional shape (e.g., radius).

Optionally, one or more MAPs are changed in coordination with change in geometry and/or geometrical appearance. Adjusted MAPs optionally include, for example, those that can be modified to show increasing "redness" of the tissue with time to indicate swelling, "whiteness" or "greyness" to indicate loss of perfusion, color change to indicate change in temperature, etc.

As another example: in some embodiments, geometrical effects are applied to indicate contractile state (for example, of cardiac muscle, or gastrointestinal tract motion). Optionally, simulations of contraction are triggered by measurements of heartbeat and/or pulse phase, and/or of autonomic nervous system activity. The geometrical effects are preferably simulated to be in synchrony with what is expected to be actually occurring in the tissue that the simulation describes. However, the simulation is optionally different from reality in one or more respects; for example, amplitude is optionally adjusted. Larger-adjusted amplitude potentially emphasizes activity (e.g., vasoconstriction is exaggerated for clarity); smaller-adjusted amplitude potentially reduces distracting effects of activity (e.g., heart contraction is shown with reduced amplitude).

In some embodiments of the invention, dynamic adjustment of heart size in a rendered view of a simulated scene is based on heart rate. Optionally, this is implemented by dynamic adjustment of the geometrical rendering data representing the heart shape. In some embodiments, the adjusting comprises adjusting a static size of one or more heart chambers (e.g., a lumenal volume of the heart chambers, and/or a lumenal dimension of the heart chambers). In some embodiments, the adjusting comprises selecting a range of heart chamber sizes simulated cyclically over the course of each heartbeat cycle, e.g., between changing minimum and/or maximum sizes.

In some embodiments of the invention, the adjustment of heart chamber size to larger or smaller sizes is accompanied by corresponding inverse adjustment of heart wall sizes to smaller or greater thicknesses.

A potential advantage of these adjustments is to increase an accuracy and/or precision with which an intrabody probe (and in particular, an intracardial catheter probe) can be positioned, and/or with which the position of such a probe can be determined. In particular, positioning precision/accuracy with respect to one or more particular regions of heart wall tissue is potentially improved; for example, a nearest and/or a pointed-at region of heart wall tissue. A pointed at location is located along a longitudinal axis extending through the probe tip.

This in turn potentially increases certainty of achieving targeted effects of treatment administration (e.g., ablation), and/or of evaluating those treatment effects. Adjustment of a display to maintain an accuracy of positioning of the intracardial probe relative to the heart is implemented, in some embodiments, using one or more of the following methods. Optionally, positioning changes of a probe relative to a heart wall due to heart size changes are at least partially represented to an operator by simulating relative movements and/or scaling of a rendered representation of an intrabody probe in a display, while suppressing at least part of the size changes undergone by the actual heart chamber represented in the display. For example, if heart chamber beats are at least partially suppressed, then changing actual probe position relative to the beating heart chamber walls is optionally displayed by movements of the probe itself. Optionally, for example, if inter-pulse heart chamber size changes (e.g., due to heartbeat rate changes) are at least partially suppressed: scaling of detected intracardial probe movements is adjusted in a display so that relative positions of heart wall and probe remain synchronized between the actual tissue and probe pair, and a display of a simulated tissue and probe pair.

In some embodiments, the wave pattern to be simulated is determined at least in part from direct measurements of impulse wave propagation. In some embodiments, the wave pattern is simulated from a generic heart tissue or other tissue model. Optionally, the wave pattern is adapted according to knowledge about tissue state, for example, to indicate regions of weak and/or slow propagation attributed to states of fibrosis, perfusion state, and/or denervation. Optionally, moreover, the degree of impulse transmission is itself modulated in simulations managed by physiology simulator 1114; for example, to reflect transmission effects of treatment activities such as lesioning, tissue cooling, injections, etc.

At block 122, in some embodiments, the current state of the geometry and/or geometrical appearance (optionally including changes to MAPs) is rendered to a visual representation of the tissue with which the interaction occurred. In some embodiments, the rendering makes use of 3-D graphics engine, for example as described in relation to display module 1130, and/or in relation to FIG. 8 and/or Table 1.

At block 124, in some embodiments, the timer is incremented.

At block 126, in some embodiments, a decision is made as to whether the loop is to continue (returning to block 120), or is terminated (stopping the flowchart). Time-evolving geometry and/or geometrical appearance optionally evolve, for example, cyclically (for example, repeating a movement pattern), transiently (disappearing at the end of a generation cycle, for example, in a simulation of cooling from a heated condition or re-warming from a cooled condition), and/or to a new steady-state appearance (for example, edema that develops to a fully developed state during a period after ablation, and then persists beyond the period during which the tissue is simulated).

It should be understood that sensing feedback is optionally integrated with the flowchart of FIG. 1B to create semi-open/semi-closed loop simulation: periods of open loop simulation producing results (e.g., geometrical effects) that are periodically verified, guided, and/or corrected according to sensed data. In some embodiments, for example, simulation of developing edema optionally proceeds independently as long as no further sensing data characterizing the edema state is available. However, if edema state is measured at some midpoint of the simulated edema time-course (for example, by use of dielectric measurements), then the simulation is optionally adjusted mid-course to reflect the sensed data. Adjustment is optionally immediate, and/or includes a period of interpolated adjustment (which potentially helps maintain the sense of presence in rendered views of the simulation scene).

Modes of Simulating Geometrical Effects

Cross-Sectional Perspective Views of Single-Lesion Progress

Reference is now made to FIGS. 2A-2E, which illustrate a 3-D rendered display for indicating lesioning status to an operator, according to some exemplary embodiments of the present disclosure. FIGS. 2A-2E show a sequence of visual renderings of a single lesion over the course of the operation of an RF ablation probe to create it. This provides an example of how adjusted geometry and/or geometrical appearance can be used (optionally together with adjustment of MAPs) to convey to an operator a direct understanding of how use of an ablation probe is affecting target tissue.

In appearance, FIGS. 2A-2E comprise images (rendered in some embodiments in the rendering pipeline 1230 of a 3-D graphical game engine 1200) of an RF ablation probe 202 (corresponding, in some embodiments, to catheter probe 11, wherein treatment element 8 is an ablation electrode, and treatment controller 13 operates to supply ablation energy to the RF ablation probe 202) and its position relative to tissue 205 targeted for ablation (e.g., part of body tissue region 7). Optionally, the rendering is in color, and/or otherwise using applied MAPs conveying the vital appearance (e.g., properties of roughness, specular reflection, etc.) of the tissue (black and white is shown herein for purposes of illustration). In some embodiments, RF ablation probe 202 is implemented as an object 1224 belonging to scene elements 1220 (FIG. 8). Tissue 205 is optionally implemented as terrain 1221 or an object 1224 belonging to scene elements 1220.

FIG. 2A, in some embodiments, shows the moment of initial contact between probe 202 and tissue 205. Optionally, this view is triggered when contact is sensed by a sensor on the probe, such as a force sensor (an example of an "other sensor" 14) and/or dielectric sensing of contact (e.g., via dielectric property analyzer 22). The triggering, mediated in some embodiments by interaction analyzer 21 (and optionally taking advantage of a collision detection service 1213 of a game engine 1200), is optionally visually implemented as a jump from a wider angle view with the probe out of contact to a close-up of the probe contacting tissue. Optionally, transition from no-contact to contact (or vice versa) is shown by a short bridging animation. In some embodiments, continuous sensing of probe position and/or probe distance to the tissue wall (for example, by a position sensing subsystem comprising sensing electrodes 3, body surface electrodes 5, field generator/measurer 10, and/or position analyzer 20 and/or position tracker 1107) allows any jump in a sensed transition between contact and non-contact to be smoothed out using actual position data.

Figure 2B:
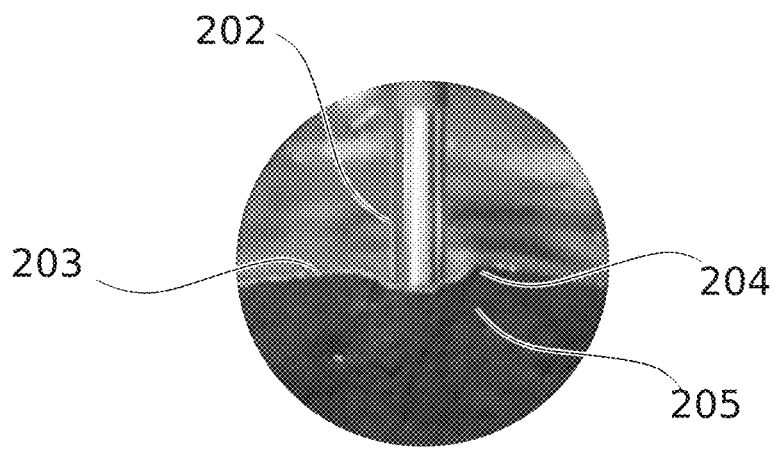
Figure 2C:
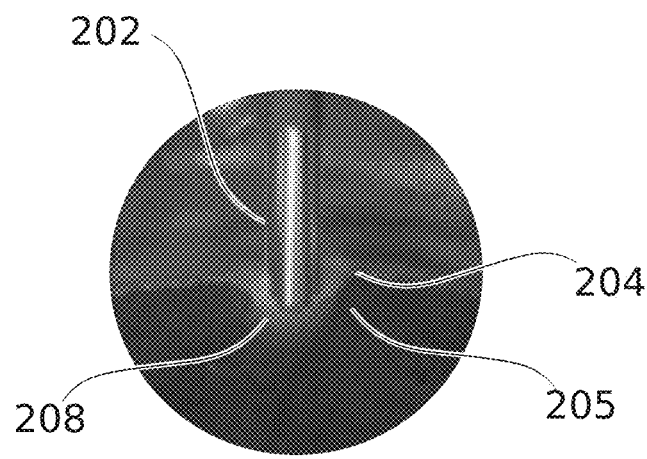

FIG. 2B, in some embodiments, includes a visual indication of increased contact pressure between the tissue 205 and probe 202 comprising an indented region 204. In FIG. 2C and then FIG. 2D, the deeper indented region 204 shows that pressure has been increased still further. Optionally, the geometry and/or geometrical appearance modifications indicate sensed and/or calculated contact pressure; the appropriate transformation being calculated, for example, by contact physics simulator 1111 (which may in turn take advantage of motion physics services 1212 and/or collision detection service 1213 of game engine 1200). Although preferably modeled based on sensed contact quality and/or force data, distances of the indentation deformation need not be exactly corresponding to deflection distances in the real tissue. Rather, the visual degree of indentation shown is optionally considered as a proxy indicator for when the probe is out of contact, in poor contact, in a good position to ablate, and/or exerting excessive force on the tissue. Optionally, tissue 205 is shown in cross-section.

This has a potential advantage for allowing the indentation size to be clearly seen (as a deflection of the surface boundary 203). Optionally, the cross-sectional view also displays information about achieved lesion parameters such as lesion depth and/or lesion transmurality. Where cross-section is shown, transformation of geometrical position data is preferably used to show indentation changes. Geometrical appearance changes (e.g., by manipulation of normal mapping) are optionally used as well; but preferably not used alone, since the edge-on view of a cross-section highlights the spatial position of surface contours.

Additionally or alternatively, in some embodiments of the invention, transparency effects are applied to allow seeing into a targeted volume of tissue. For example, before ablation begins, a local region of tissue selected by the position of probe 202 is shown with increased transparency. Optionally, as portions of the tissue become lesioned, they are represented in simulated display as more opaque; creating an ablation "island" that directly shows the progress of lesioning. A potential advantage of the transparency approach is to allow representation of lesioning progress from any arbitrary 3-D point of view including the targeted tissue region.

Figure 2D:
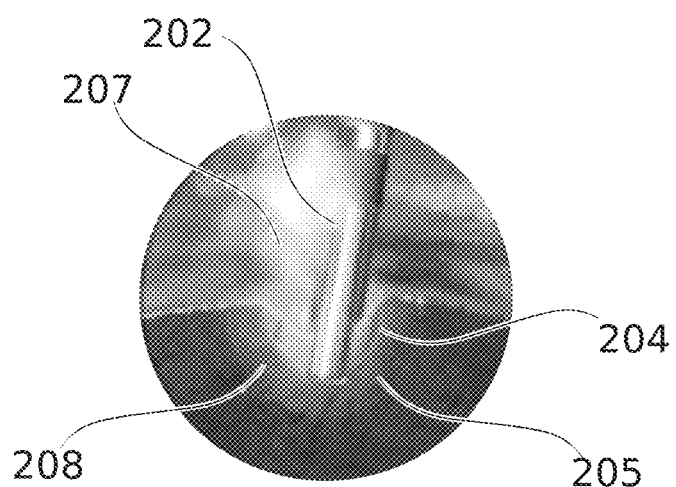
Figure 2E:
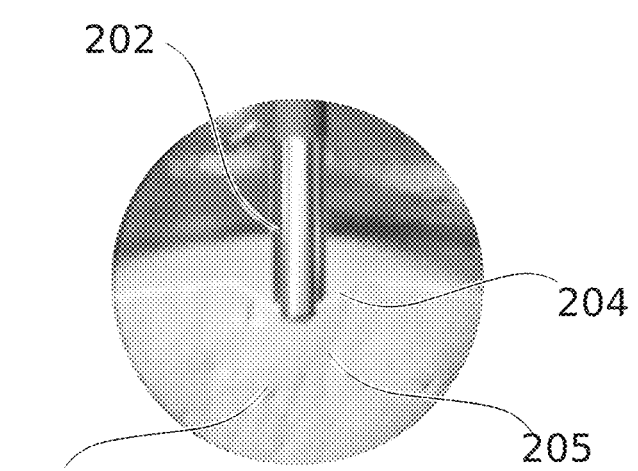

In FIG. 2C, in some embodiments, there has been a slight increase in sensed contact (shown by increased indentation of indented region 204), and ablation by delivery of RF energy to the tissue from probe 202 has begun. A superficial lesioned portion 208 of tissue 205 is now shown, for example, in a lighter shade (in color, lesioned portion 208 is optionally colored a light grey compared to darker red vital tissue). As lesioning proceeds (for example, to the intermediate state indicated in FIG. 2D, and finally to the completed lesion 209 in FIG. 2E), lesioned portion 208 gradually increases in extent and/or degree of MAP change from the pre-lesioned state. FIG. 2D also indicates an increased pressure of contact by an indented region 204 in the tissue, while FIG. 2E shows pressure reduced. Optionally, the geometrical deformation changes as tissue ablation proceeds (even for a fixed pressure), for example to indicate changes in tissue elasticity and/or volume.

In some embodiments, this progression is based on inputs describing the operation of the treatment modality (ablation, in the illustrated example). For example, inputs describing power, duration, and/or contact quality are factored into a simulation (e.g., by an ablation physics simulator 1112) linked to how the tissue is displayed in its geometrical and/or material appearances. Optionally, operation of an ablation physics simulator 1112 includes thermal modeling (thermal simulation), based on local tissue region properties, for example, of local tissue type, thickness, thermal conductivity, and/or thermal exchange (e.g., between tissue and flowing blood). In some embodiments, at least part of the information providing local tissue type and/or thickness is obtained based on dielectric properties calculated from measurements of an alternating electromagnetic field obtained from a sensing electrode 3 at or near the position of the lesion 209.

In some embodiments, calculated dielectric properties are used as indications of lesion state (e.g., size, transmurality, completeness and/or irreversibility), for example as described in International Patent Application No. PCT/IB2016/052690, the contents of which are incorporated by reference herein in their entirety. In in vitro studies, accuracy of transmurality has been found to be about ±1 mm. In prospective in vivo studies, 100% sensitivity and specificity in predicting lesion transmurality was found, while in humans, at least 90% specificity and sensitivity was found. Specificity is the percentage of actually well-ablated areas that were dielectrically identified as well-ablated; sensitivity is the percentage of actually partially ablated areas that were dielectrically identified as partially ablated.

Additionally or alternatively, the progression during lesioning is based on inputs describing sensed data reflecting one or more treatment effects, for example, measured temperature and/or changes in dielectric properties as tissue begins to break down. In general, probe-based temperature sensing, where available, is limited in resolution and/or depth, so that completely sensing-based adjustment may be difficult or impossible to obtain. However, sensed data may nevertheless be used as input to an ablation physics simulator 1112 that extrapolates lesion state through a 3-D block of tissue. Optionally, the extrapolated state is used as a corrective and/or calibrating input to an ablation physics simulator 1112.

In some embodiments, one or more additional indications of house lesioning is proceeding are provided as part of the rendered image. For example, in FIG. 2D, "steam" 207 is shown arising from the lesion point. Optionally, this is an indication that temperature has reached (and/or is maintained at) a certain threshold. The threshold may be, for example, a threshold at which lesioning occurs, a threshold above which a danger of effects such as steam pop or charring occurs, or another threshold. Different characteristics of the "steam" could be used, for example, conversion to black (or increasingly black) "smoke" in case of increased danger of excessive heating. In some embodiments of the invention, such steam- and/or smoke-like effects are implemented using a particle system facility provided by a graphical game engine.

Simulation of Tissue "Tenting"

Reference is now made to FIGS. 3A, 3D, 3G, and 3J, which schematically represent a sequence of rendered views of a rendered catheter probe 11A (representing a catheter probe 11) passing through a rendered tissue wall region 50, according to some embodiments of the present disclosure. Reference is also made to FIGS. 3B, 3E, 3H, and 3K, each of which schematically represents a graph of position versus time and measured contact versus time for the catheter probe 11 rendered as rendered catheter probe 11A of FIGS. 3A, 3D, 3G, and 3J, according to some embodiments of the present disclosure. Additionally, reference is made to FIGS. 3C, 3F, 3I, and 3L, which schematically represent an ultrasound image at a cross-section of a heart at the atrial level, and corresponding to the sequence of FIGS. 3A, 3D, 3G, and 3J, according to some embodiments of the present disclosure.

In some embodiments of the invention, the geometry of a three-dimensional simulation of a tissue wall region 50 is updated for displaying at a motion frame rate. The frame updating may be based on information received from one or more sensing modalities. The information may be received as catheter probe 11 interacts with a tissue wall. The two figure series of FIGS. 3B, 3E, 3H, and 3K and FIGS. 3C, 3F, 3I, and 3L represent different examples of sensed inputs related to tissue-catheter probe interactions, based on which (in any suitable combination) the tissue deformations of FIGS. 3A, 3D, 3G, and 3J are simulated.

The sensing modalities optionally comprise modalities that are non-imaging in nature (e.g., catheter probe position tracking data, and/or probe-sensed parameter time-course data), and/or comprise images giving incomplete view coverage of the simulated tissue region (for example, cross-sectional images). New sensing data is optionally acquired faster, slower, or at the same rate as the simulation appearance is updated.

Simulation and visualization updating is optionally in correspondence with states indicated by recently sensed data. For example when sampling is slow and/or intermittent, the current simulation state is optionally extrapolated from recent data according to one or more trends therein. Optionally, simulation updating is delayed from the acquisition of real-time data (for example, delayed to a buffer of at least two recent samples, and/or for example, by up to about 250 msec), which optionally allows smoothing interpolation between actually measured sensing data points in exchange for a certain amount of lag.

The X-axes of graphs 310 of FIGS. 3B, 3E, 3H, and 3K represent relative time. The Y-axes overlappingly represent sensed catheter probe position advance above a baseline position 311 (dashed lines including points 312, 314, 316, and 318), and a measure of sensed catheter probe-tissue contact (solid lines including points 313, 315, 317, and 319). The measure of sensed catheter probe-tissue contact may include, for example, force and/or dielectrically measured contact quality. The position of contacted region 302 of the actual tissue wall portion represented by rendered tissue wall region 50 relative to catheter tip 301 is represented in the graphs by dotted line 309.

In some embodiments of the invention, probe-tissue contacts causing and/or represented by geometrical tissue deformations within the body are measured using one or more sensing modalities (for example, sensing by a force sensor, by sensing of impedance properties, or another sensing modality) that are only partially indicative of the overall geometrical effects of the contact. In some embodiments, the one or more sensing modalities provide information as to the variation over time of a limited number of parameters communicated in the interaction data; for example, one, two, three, or more parameters.

For example, in some embodiments, sensing information that encodes position of probe 11 is available. The position of probe 11 may be indicated by the interactive information absolutely and/or relative to the tissue portion represented by rendered tissue region 50. In some embodiments, the sensing information may be indicative of contact quality and/or contact force measured to exist between probe 11 and the tissue portion represented by rendered tissue region 50. In some embodiments, these measurements are used to guide changes made to simulated tissue region 50 and rendered probe 11A, and the model rendered in turn to a sequence of images that visually simulate geometrical effects associated with the sensed information.

In some embodiments, the simulated model comprises a mechanical model of a tissue wall, including, for example, properties of tissue wall thickness, elasticity, density, velocity, and/or viscosity suitable to the tissue being simulated. Simulation of deformations optionally comprises applying a force commensurate with sensed forces and/or positions. Preferably, simulated geometrical effects are generated to faithfully visualize those effects that are actually occurring. In such embodiments, a mechanical model of the tissue wall is preferably provided with parameter values yielding realistic-looking behavior in reaction to applied simulated force and/or displacement. Graphical game engines commonly expose services for the simulation of physical interactions of scene elements, providing a potential advantage for ease of implementation.

Optionally or additionally, simulated geometrical effects may convey to an operator information about the contact, even though actual geometrical distortions (e.g., geometrical distortions introduced by touching contact with a probe, which may comprise pressing on tissue by the probe) are potentially different than the simulation shows: e.g., smaller in size, and/or modeled to simply indicate stages in deformation, without quantitative fidelity. In such embodiments, a simulated mechanical model is optionally implemented with parameters giving model behaviors that are potentially different from the actual case. Optionally, the model is implemented more simply; for example, as a mapping of a range of geometrically distorted wall shapes to one or more corresponding ranges of sensed input values.

Additionally or alternatively, in some embodiments, image information at least partially describing geometrical changes is available to the operator. The image information may be spatially incomplete: for example, an ultrasound cross-section that illustrates deformation in a planar cross-section of the tissue wall portion that an intrabody probe is penetrating. In some embodiments, an imaging modality other than ultrasound is used, for example, X-ray fluoroscopy. Preferably, the imaging modality provides images at a rate sufficient to guide manipulation of the catheter probe 11, but this can optionally be a rate below motion frame rate; for example, at least 2-5 Hz. FIGS. 3C, 3F, 3I, and 3L represent a time sequence of ultrasound images measured from an ultra sound probe located in the lumen of a left atrium 321 (about at the apex of ultrasound images 320), as a probe 11 crosses into the left atrium 321 from a right atrium 322. In the case illustrated, rendered tissue wall region 50 and/or imaged tissue wall portion 50B represent a tissue wall portion comprising an interatrial septum which is to be crossed by a catheter probe 11 at a contact region corresponding to contacted region 302, for example the foramen ovale (which may be a weak spot in the interatrial septum, or even a residual opening between the two atria). Although the ultrasound images 320 do not simultaneously show in imaged tissue wall portion 50B the whole three dimensional structure of the tissue wall portion represented by rendered tissue wall region 50, they potentially do reveal partial information about how the wall is deforming. In some embodiments, the partial information is used in a simulation of tissue-wall interaction dynamics to show a live-updated 3-D view of the tissue wall. For example, a curve extending through the image plane along the visualized extent of the interatrial septum is optionally used as a guide, to which a simulated tissue wall geometrical distortion in that plane is fit; and moreover, may be used as a boundary condition to which out-of-plane tissue wall geometrical distortions are also constrained.

Turning now to the images in sequence, FIG. 3A represents a rendered view showing the tip 301 of rendered catheter probe 11A approaching the contacted region 302 of rendered tissue wall region 50. Rendered tissue wall region 50 is shown in cross section; however, it should be understood that in other examples (not drawn) it may be shown from any other appropriate view angle. Optionally or additionally, rendered tissue wall region 50 is shown opaque, transparent, or in any suitable combination of the two.

In FIG. 3A, the rendered tissue wall region 50 is shown in what is optionally its default and/or resting state geometry: for example, a geometry determined from a segmentation of an earlier MRI and/or CT scan (it should be understood that contact-independent behaviors such as periodic heart contractions are optionally superimposed on a default geometry). In some embodiments, based on the data of FIG. 3B, a simulator is configured to recognize that this non-interacting geometry default should be shown. For example, a contact sensing parameter value 313 optionally indicates that there is no contact force exerted. Additionally or alternatively, the distance between catheter probe position 312 and the expected (optionally, sensed) wall position trace at dotted line 309 indicates that there is not yet any contact.

Additionally or alternatively, the ultrasound image of FIG. 3C shows no deformation of rendered wall region 50 in the vicinity of target contacted region 302, and/or shows a separation between rendered wall region 50 and rendered catheter probe 11A. Use of 3-D rendering to augment ultrasound imaging of tissue wall deformation (for example, as shown in FIG. 3C) has the potential advantage of converting a relatively abstract-appearing (cross-sectional, black and white, visually noisy) display of ultrasound-imaged anatomical structures into a solid looking indication of how forces from a catheter are interacting with a heart wall, on the basis of which the penetration operation can be guided.

In the second set in the sequence (FIGS. 3D-3F), wall contact has begun, as shown (FIG. 3D) by the deformation of the rendered tissue wall region 50 in contact with catheter probe tip 301. Optionally (FIG. 3E), this simulation is generated to track the rising value of sensed contact (e.g., at point 315). Additionally or alternatively, the simulation is generated to track the forward movement of the probe tip 301 to point 314; optionally, the simulation scene is generated to track the forward movement with respect to expected or measured wall position trace at dotted line 309. Additionally or alternatively, deformation of the imaged tissue wall portion 50B in an ultrasound image (FIG. 3F) is used as a constraint to guide how the rendered tissue wall region 50 is geometrically distorted in 3-D. Optionally, contact between imaged tissue wall portion 50B and catheter probe 11 is determined and/or verified from the ultrasound image as well.

In the third set in the sequence, (FIGS. 3G-3I), deformation has reached a maximum before catheter probe 11 breaks through the rendered tissue wall region 50 at contacted region 302 (foramen ovale). In the fourth set in the sequence (FIGS. 3J-3L), rendered catheter probe 11A is shown having broken through the rendered tissue wall region 50. From the sensing data of FIG. 3K, the breakthrough is optionally inferred by the sudden drop in sensed contact, optionally in concert with the continued advance of the catheter probe 11. Additionally or alternatively, the breakthrough is inferred from the sudden increase in distance between the catheter probe 11 and the actual tissue wall (inferred, for example, from a sudden change in the dielectric environment of an electrode associated with probe tip 301). In the ultrasound image of FIG. 3L, the breakthrough is optionally inferred from a relaxation of the geometrical distortion of imaged tissue wall portion 50B, and/or by the observation of a portion of catheter probe 11 extending on the other side of the imaged tissue wall portion 50B.

Contact Simulation—Example of Simulation

Figure 10A:
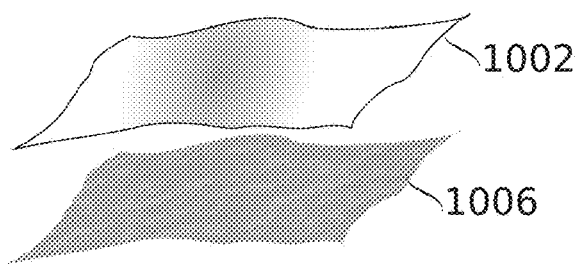
FIGS. 10A-10B illustrate normal mapping superimposed on a tissue region in order to provide the geometrical appearance of a swelling, according to some embodiments of the present disclosure.
Figure 10A:
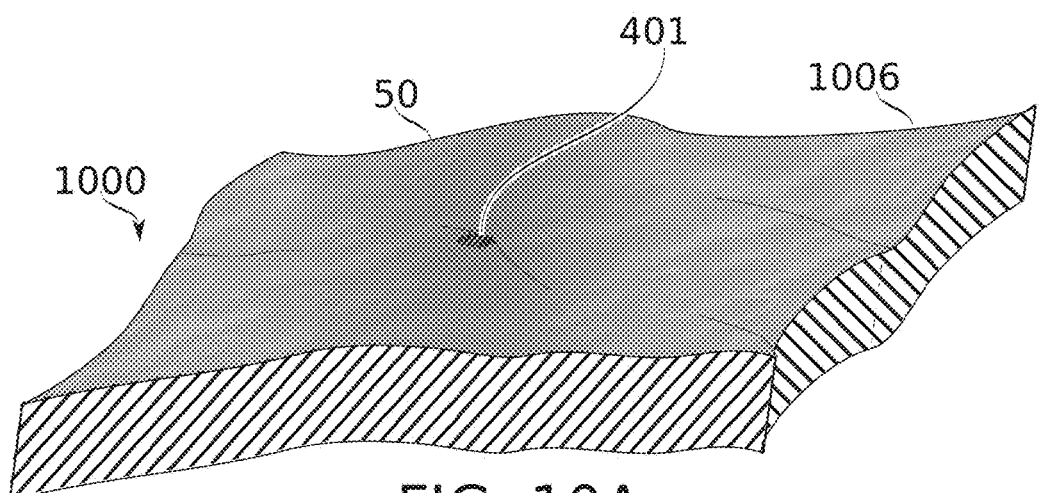
Figure 10B:
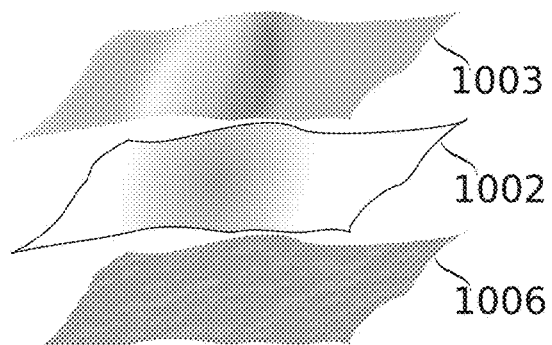
Figure 10B:
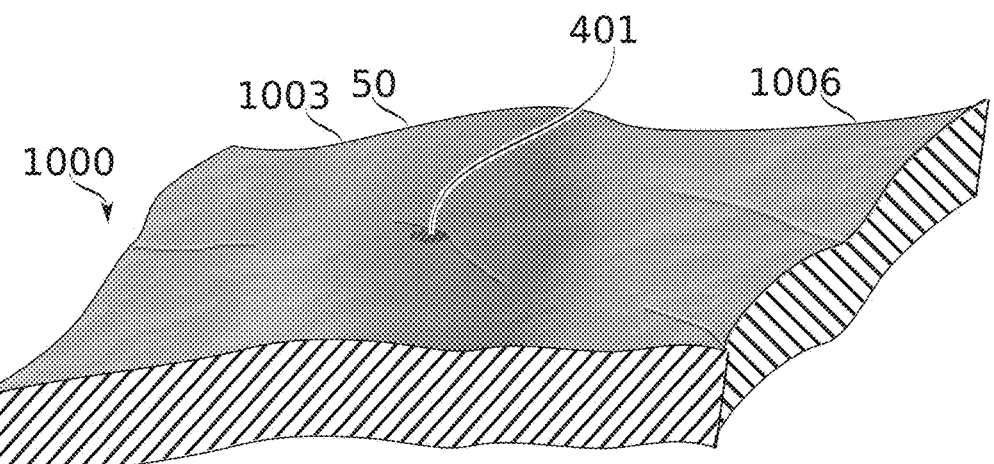
Figure 10C:
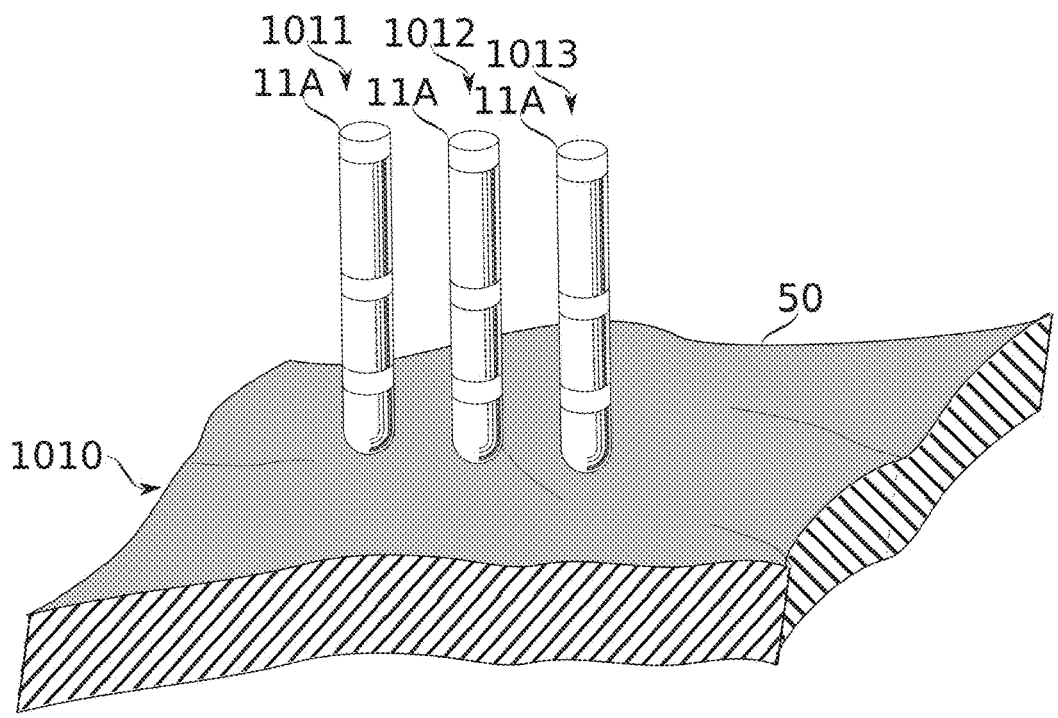
FIGS. 10C-10D schematically represent aspects of geometrical deformation of a tissue region in touching contact with a catheter probe, according to some embodiments of the present disclosure.
Figure 10D:
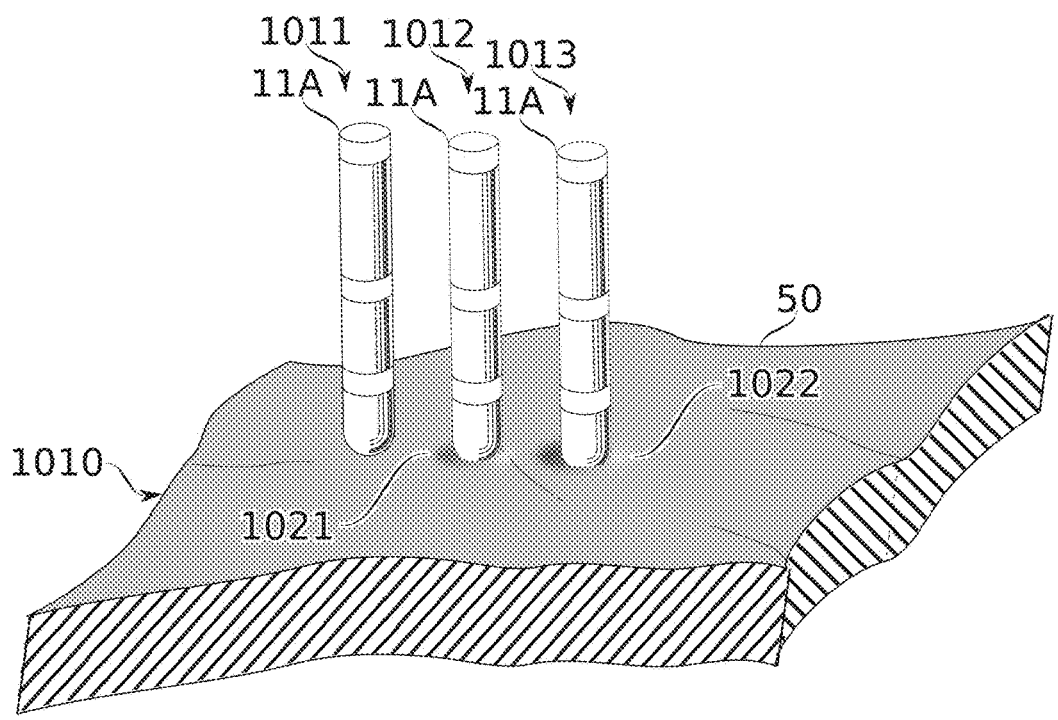

Reference is now made to FIGS. 10C-10D, which schematically represent aspects of geometrical deformation of a rendered tissue region 50 in contact with a rendered catheter probe 11A, according to some embodiments of the present disclosure. In some embodiments of the invention, displayed interactions of a rendered catheter probe 11A with a rendered tissue wall region 50 include geometrical effects which look like deformations of the tissue wall that visually convey the forces of their interaction.

Full geometrical deformation, including mesh deformation, is described herein in relation to the examples of FIGS. 2A-2E and 3A-3L. In FIGS. 10C-10D, a different mode of indentation is shown, wherein relatively limited (and, potentially, computationally less expensive) geometrical deformation is simulated by the use of one or more rendering techniques such as normal mapping, depth mapping, shadow mapping, depth of field simulation, and the like.

In FIG. 10C, rendered catheter probe 11A is shown in a sequence of positions relative to the rendered surface 1010 of a rendered tissue region 50 (optionally, rendered surface 1010 is rendered with the use of any suitable MAPs to provide it with a tissue-like visual appearance). Apart from the obvious lateral displacement, each position 1011, 1012, 1013 is also vertically displaced with respect to the tissue surface. However the only visual indication that positions 1012 1013 actually contact the surface (while 1011 does not) is a slight successive truncation of the catheter probe tip 301.

In FIG. 10D, all the elements of FIG. 10C and their relative positions remain the same, but there is shown in addition the effects of manipulation of the surface normal map in region 1021 and indentation region 1022, assuming a light source that is to the left and somewhat behind the plane of the drawing (normal mapping is described in relation to FIGS. 9A-9B). The normal map manipulations have been chosen to give the appearance of geometrical changes—specifically, to indicate indentations in rendered surface 1010. In some embodiments of the invention, this geometrical appearance change is optionally triggered by any suitable input related to probe-tissue contact, for example, contact force measurements, dielectric contact quality measurements, and/or relative position measurements of tissue and probe. Optionally, the normal map is also adjusted to reflect contact angle, for example, stretched along a dimension of elongated contact. Since no change in the underlying 3-D object geometry is required in order to produce this effect, there is a potential advantage for computational efficiency and/or reduced complexity of implementation compared to manipulation of the full 3-D geometry.

The normal-mapped mode of representing geometrical deformation is of potential use to an operator for helping to gauge contact quality before lesioning, particularly in views having a substantial elevation angle above the contacted surface. Optionally, views using normal mapping-type indentation are presented alongside views where 3-D geometrical distortion is used (for example, in cross-section, as discussed in relation to FIGS. 2A-2E). Optionally, normal mapping is used to exaggerate 3-D geometrical deformation, for example, to potentially increase emphasis and/or clarity.

Physiological Simulation—Example of Simulation

Reference is now made to FIGS. 4A-4D, which schematically represent aspects of geometrical deformation of a rendered tissue region 50 due to an internal change such as edema, according to some embodiments of the present disclosure. Reference is also made to FIGS. 10A-10B, which illustrate normal mapping superimposed on a rendered tissue region 50 in order to provide the geometrical appearance of a swelling, according to some embodiments of the present disclosure. Further reference is made to FIGS. 5A-5B, which schematically represent global geometrical deformation of a tissue structure, for example, due to hydration state and/or more global edema than the example of FIGS. 4A-4D, according to some embodiments of the present disclosure.

Figure 4A:
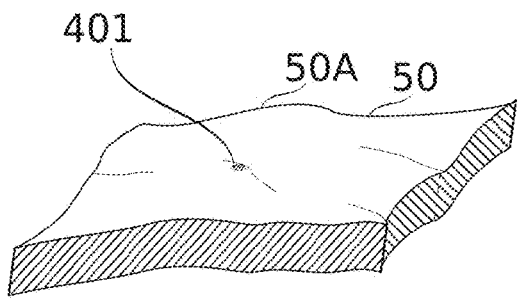
FIGS. 4A-4D schematically represent aspects of geometrical deformation of a tissue region due to an internal change such as edema, according to some embodiments of the present disclosure.
Figure 4B:
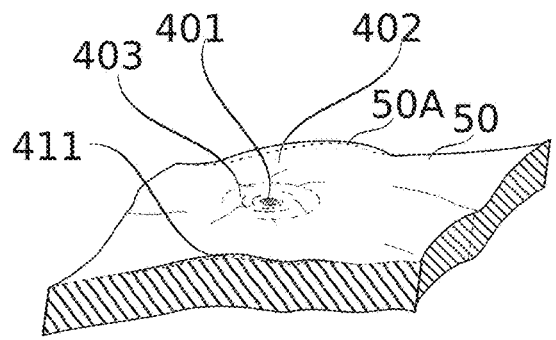
Figure 4C:
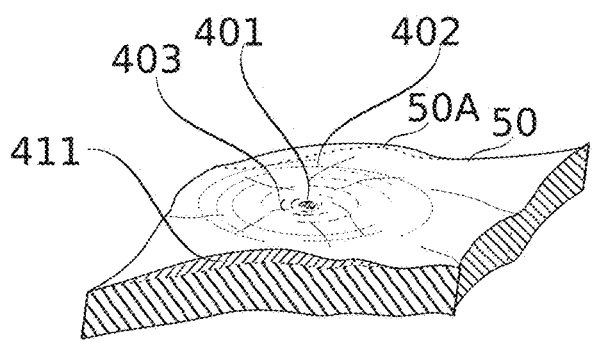
Figure 4D:
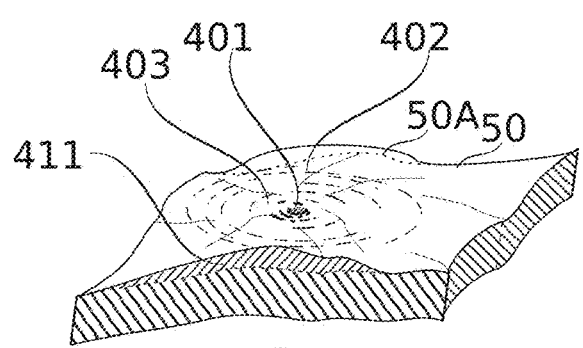

In FIG. 4A, lesion 401 represents a recently formed lesion, for example, an RF ablation lesion. Over the course of a few minutes after RF ablation, tissue potentially reacts with a swelling response. In some embodiments of the invention, the swelling response is simulated (for example, as a function of time according to the method of FIG. 1B, and/or based on measurements such as dielectric measurements that provide edema data) by one or both of increasing thickness in a region 403 surrounding lesion 401 (thickness changes can also be seen in the changing thickness of region 411 between FIGS. 4B-4D; comparison also can be made to the baseline surface boundary 50A), and a change in color and/or texture in region 402 (represented by the partial rings in the drawing).

FIGS. 10A-10B illustrate how normal mapping can be used to potentially enhance the appearance of changes in a tissue, for example as a result of treatment and/or injury. Lesion 401 again indicates a recently formed lesion. In FIG. 10A, a surface is rendered as combination image 1000 by combining baseline surface texture 1006, with an injury response overlay 1002. In the combination image 1000 (in the example shown, the method of combination is partial transparency overlaying; optionally, another method of combining within a rendering pipeline 1230 is chosen) the injury response is detectable, but not clearly delineated. FIG. 10B adds to this an overlay 1003 generated from a normal map (assuming a light source to the left of the page) that describes a swelling in the region of the injury response. By changing the geometrical appearance of the tissue (though not necessarily the 3-D tissue geometry data itself), the injured region is potentially emphasized in the resulting view. It is to be understood that the 3-D geometry swelling of FIGS. 4A-4D are optionally combined with the normal mapping of FIGS. 10A-10B.

Figure 5A:
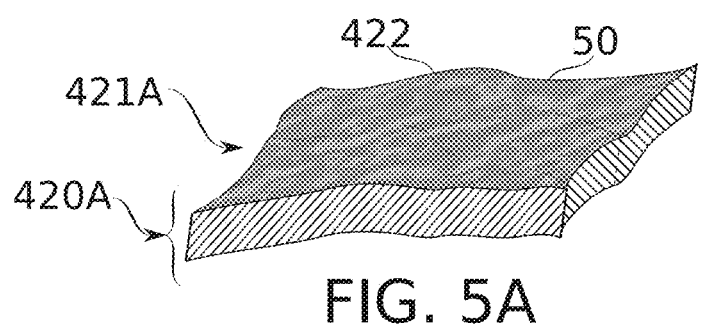
FIGS. 5A-5B schematically represent global geometrical deformation of a tissue structure, for example, due to hydration state and/or more global edema than the example of FIGS. 4A-4D, according to some embodiments of the present disclosure.
Figure 5B:
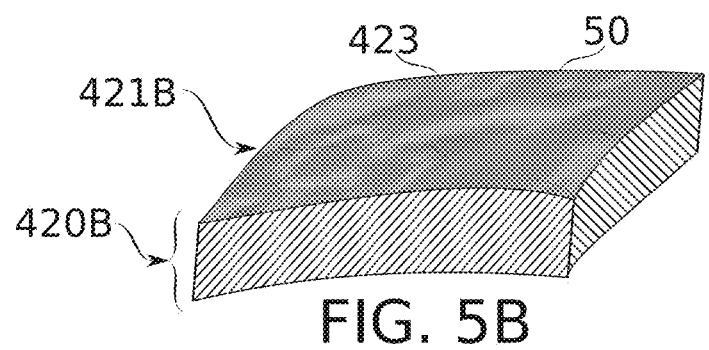

In FIGS. 5A-5B, generalized tissue thickening is represented by the change in tissue dimension between baseline thickness 420A and swollen thickness 420B. The thickening is optionally derived from measurements and/or extrapolation, for example, according to one or more of the methods of FIGS. 1A-1B. Optionally, other changes are also made to represent tissue changes. As can be seen from the cross-sectional borders 422, 423 of tissue region 50, the 3-D geometry of rendered tissue region 50 is optionally smoothed out with increasing swelling. Additionally or alternatively, normal mapping across the extent of surfaces 421A, 421B is adjusted as a function of swelling: for example, simulated wrinkles used to texture surface 421A are optionally smoothed and/or stretched, for example to indicate a tauter appearance as at texture surface 421B.

Example of Probe-Determined Camera Perspective

Figure 11A:
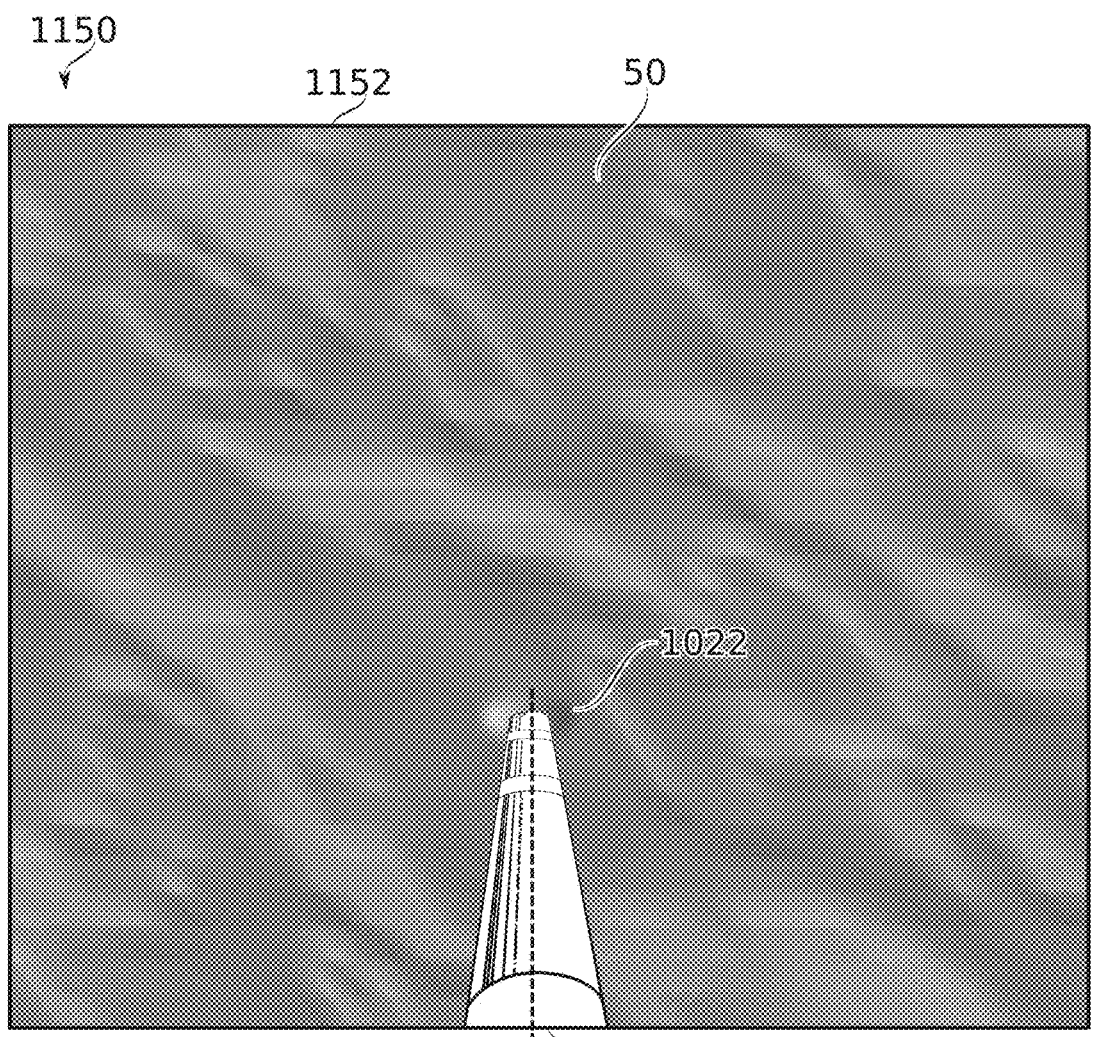
FIG. 11A schematically illustrates a rendered image rendered from a camera viewpoint looking at tissue region along an axis parallel to an intrabody probe; according to some embodiments of the present disclosure.
Figure 11B:
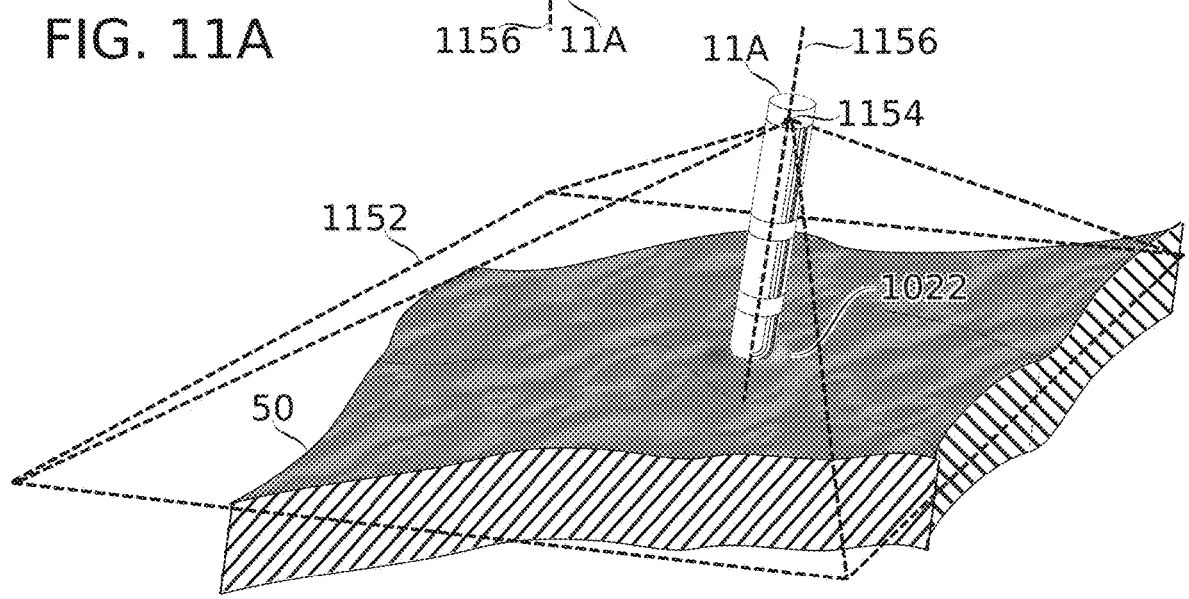
FIG. 11B schematically illustrates a field of view projected from camera viewpoint, including indication of axis, according to some embodiments of the present disclosure.

Reference is now made to FIG. 11A, which schematically illustrates a rendered image 1150 rendered from a camera viewpoint 1154 looking at rendered tissue region 50 along an axis 1156 parallel to a rendered catheter probe 11A, according to some embodiments of the present disclosure. Reference is also made to FIG. 11B, which schematically illustrates a field of view 1152 projected from camera viewpoint 1154, including indication of axis 1156, according to some embodiments of the present disclosure. Indentation region 1022 indicates a region of touching contact between probe 11 and rendered tissue region 50. FIG. 11A and FIG. 11B comprise views looking onto the same simulation scene.

In some embodiments, a camera viewpoint 1154 is defined (e.g., as part of the definition of a camera 1223, FIG. 8) to be positioned on or near the body of a catheter probe 11, and looking along an axis 1156 which is substantially parallel to the rendered catheter probe 11A (termed a "probe-mounted" view herein). Insofar as the system tracks (using measured position) the location and orientation of the actual catheter probe 11 which the rendered orientation of rendered catheter probe 11A simulates, camera viewpoint 1154 also tracks (by adjustment to match the orientation of the rendered catheter probe 11A) the orientation of the actual catheter probe 11.

It may be noted that rendered catheter probe 11A appears in rendered image 1150 in a position similar to the position of hand-held tools seen in some "first-person" games, wherein a tool is shown on the screen in a position as if held before otherwise unseen avatar whose eyes define the camera position. In some embodiments of the present invention, this viewpoint configuration provides a potential advantage for obtaining a clear view of the field of operation of the probe, e.g., when it contacts tissue.

Optionally, registration between the probe and the viewpoint may comprise any other suitable combination of position and orientation. For example, looking back along a catheter is potentially useful for obtaining a sense of what freedom exists in how the catheter probe can be presently positioned. Looking at the catheter itself from a more distant position potentially provides an improved sense of how the catheter relates to its overall surroundings. In some embodiments, viewpoint optionally shifts (automatically and/or under manual control) depending on what action is being performed; for example, a probe-mounted view like that of FIG. 11A is optionally used for selection of where a probe should be advanced to contact tissue, while a vantage point more distant from the probe may be selected to show details of how probe and tissue interact once contact is made (for example, as shown in the sequence of FIGS. 3A, 3D, 3G, and 3J). In some embodiments, the angular size of the field of view (area subtended within the frame of the rendered image) is selected to be larger or smaller. A larger angular size provides a potential relative advantage in helping an operator orient within a simulated environment, while a smaller angular size is optionally used to magnify details and/or reduce simulated optical distortion in the rendered view.

General

It is expected that during the life of a patent maturing from this application many relevant catheter probes will be developed; the scope of the term catheter probe is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of visually displaying effects of a medical procedure, comprising:
   receiving interaction data from an intrabody probe indicating touching contacts between the intrabody probe and a body tissue region, wherein the interaction data at least associate the contacts to contacted positions of the body tissue region;
   adjusting geometrical rendering data representing a shape of the body tissue region to obtain adjusted geometrical rendering data, wherein the adjusting is based on an indication in the interaction data of a change in the shape of the body tissue region due to the contacting;
   rendering the adjusted geometrical rendering data to a rendered image; and
   displaying the rendered image;
   wherein the rendering includes rendering a view of the intrabody probe in the rendered image.

2. The method of claim 1, wherein the intrabody probe is a catheter probe.

3. The method of claim 1, wherein the geometrical rendering data are adjusted as a function of time since a time of occurrence of an indicated contacts.

4. The method of claim 1, wherein the receiving, the adjusting, and the displaying are performed iteratively for a sequence of contacts for which interaction data is received.

5. The method of claim 1, wherein the geometrical rendering data include a representation of 3-D surface positions and a representation of surface orientations; wherein the two representations each correspond to a same portion of the shape of the body tissue region; and wherein the adjusting comprises adjusting the surface orientation representation to change a geometrical appearance in the rendering.

6. The method of claim 5, wherein the representation of surface orientation is adjusted separately from the representation of 3-D surface positions.

7. The method of claim 1, wherein the extent and degree of the adjusting model a change in a thickness of the body tissue region.

8. The method of claim 1, wherein the interaction data describe an exchange of energy between the intrabody probe and the body tissue region by a mechanism other than contact pressure.

9. The method of claim 8, wherein the adjusting comprises updating the geometrical rendering data based on a history of interaction data describing the exchange of energy.

10. The method of claim 9, wherein the exchange of energy comprises operation of an ablation modality.

11. The method of claim 10, wherein the updating changes an indication of lesion extent in the geometrical rendering data based on the history of interaction data describing the exchange of energy by operation of the ablation modality.

12. The method of claim 10, wherein the updating comprises adjusting the geometrical rendering data to indicate a change in mechanical tissue properties, based on the history of interaction data describing the exchange of energy.

13. The method of claim 9, wherein effects of the history of interaction data describing the exchange of energy are determined from modelling of thermal effects of the exchange of energy on the body tissue region.

14. The method of claim 13, wherein the modelling of thermal effects accounts for local tissue region properties affecting transfer of thermal energy between the intrabody probe and the body tissue region.

15. The method of claim 1, wherein the adjusting is as a function of time during a period of time after a time of occurrence of at least one of the indicated contacts, and comprises adjusting the geometrical rendering data to dynamically indicate development of a change in geometry of the body tissue region progressing through a plurality of different geometries during the period of time, and as a result of the contacts.

16. The method of claim 15, wherein the developed change in geometry during the period of time indicates a developing state of edema.

17. The method of claim 16, comprising geometrically distorting the rendering of the geometrical rendering data into a swollen appearance, to an extent based on the indicated development of the state of edema.

18. The method of claim 15, wherein the contacts comprise mechanical contacts, and the development of a change in geometry during the period of time indicates swelling of the body tissue region in response to tissue irritation by the mechanical contacts.

19. The method of claim 15, wherein the contacts comprise an exchange of energy between the intrabody probe and the body tissue region by a mechanism other than contact pressure.

20. The method of claim 1, wherein the interaction data indicate a geometrical distortion introduced by touching contact between the intrabody probe and the body tissue region.

21. The method of claim 1, wherein the interaction data describes injection of a substance from the intrabody probe to the body tissue region, and the adjusting comprises changing a thickness of tissue in the body tissue region, corresponding to an effect of the injection of the substance.

22. The method of claim 1, wherein the rendering is rendered from a viewpoint at least partially defined by a measured position of the intrabody probe relative to a surface of the body tissue region.

23. The method of claim 1, wherein the body tissue region comprises a tissue of at least one organ of the group consisting of the heart, vasculature, stomach, intestines, liver and kidney.

24. The method of claim 1, further comprising assigning material appearance properties across an extent of the geometrical rendering data, based on the interaction data; and wherein the displaying of the rendered image uses the assigned material appearance properties.

25. The method of claim 1, wherein the rendering comprises a rendering in cross-section of the body tissue region.

26. The method of claim 25, wherein the extent and degree of the adjusting simulate stretching of the body tissue region.

27. The method of claim 1, comprising receiving current heart rate data; wherein the geometrical rendering data represent a shape of a body tissue region comprising a heart chamber; and wherein the adjusting comprises adjusting a size of the heart chamber, based on the current heart rate data.

28. The method of claim 27, wherein the adjusting a size of the heart chamber comprises adjusting a size of a lumen of the heart chamber, based on the current heart rate data.

29. The method of claim 27, wherein the adjusting a size of the heart chamber comprises adjusting a thickness of a wall of the heart chamber, based on the current heart rate data.

30. The method of claim 27, wherein the adjusting geometrical rendering data comprises adjusting a position of the intrabody probe in the geometrical rendering data relative to a wall of the heart chamber, based on the current heart rate data.

31. The method of claim 1, wherein the interaction data indicate a contact force between the intrabody probe and the body tissue region.

32. A method of visually displaying a medical procedure, comprising:
    receiving heart rate data for a heart;
    adjusting geometrical rendering data representing a shape of the heart and a shape and position of an intracardial probe to obtain adjusted geometric rendering data;
    wherein the adjusting is based on the heart rate data to maintain an accuracy of positioning of the intracardial probe relative to the heart as average size of the heart changes as a function of a heart rate;
    rendering the adjusted geometrical rendering data to a rendered image; and
    displaying the rendered image.

33. The method of claim 32, comprising:
    receiving position data indicating the position of the intracardial probe within the heart; and
    calculating geometrical rendering data representing the position of the intracardial probe using the received position data.

* * * * *